United States Patent
Sablone et al.

(10) Patent No.: US 12,414,879 B1
(45) Date of Patent: Sep. 16, 2025

(54) METHODS AND APPARATUS FOR MAKING ABSORBENT ARTICLES HAVING A POCKET AND ABSORBENT ARTICLES

(71) Applicant: Fameccanica.Data S.p.A., Pescara (IT)

(72) Inventors: Gabriele Sablone, Pescara (IT); Fabio Passarella, Pianella (IT)

(73) Assignee: Fameccanica. Data S.p.A., Pescara (IT)

( * ) Notice: Subject to any disclaimer, the term of this patent is extended or adjusted under 35 U.S.C. 154(b) by 0 days.

(21) Appl. No.: 18/675,442

(22) Filed: May 28, 2024

(51) Int. Cl.
*A61F 13/15* (2006.01)
*A61F 13/49* (2006.01)

(52) U.S. Cl.
CPC .. *A61F 13/15593* (2013.01); *A61F 13/15626* (2013.01); *A61F 2013/49025* (2013.01)

(58) Field of Classification Search
None
See application file for complete search history.

(56) References Cited

U.S. PATENT DOCUMENTS

| | | | |
|---|---|---|---|
| 4,834,741 A * | 5/1989 | Sabee | A61F 13/49009 604/385.29 |
| 4,977,011 A * | 12/1990 | Smith | B32B 5/04 428/152 |
| 5,389,173 A * | 2/1995 | Merkatoris | A61F 13/15609 156/229 |
| 5,643,396 A * | 7/1997 | Rajala | B29C 66/81469 156/461 |
| 6,443,935 B1 * | 9/2002 | Gustafsson | A61F 13/15601 156/496 |
| 7,718,021 B2 | 5/2010 | Venturino et al. | |
| 8,182,457 B2 * | 5/2012 | Olson | A61F 13/4902 604/385.27 |
| 8,702,671 B2 * | 4/2014 | Tsang | A61F 13/539 604/385.01 |
| 8,764,922 B2 | 7/2014 | Popp et al. | |
| 8,945,326 B2 | 2/2015 | Lenser et al. | |
| 9,095,474 B2 * | 8/2015 | Nakano | A61F 13/15593 |
| 9,271,878 B2 * | 3/2016 | Nakano | A61F 13/15593 |
| 9,345,625 B2 | 5/2016 | Lenser et al. | |
| 9,468,564 B2 | 10/2016 | Popp et al. | |
| 10,085,896 B2 | 10/2018 | Lenser et al. | |
| 10,561,537 B2 | 2/2020 | Lenser et al. | |
| 10,568,775 B2 | 2/2020 | Lenser et al. | |
| 10,568,776 B2 | 2/2020 | Lenser et al. | |
| 10,575,993 B2 | 3/2020 | Lenser et al. | |
| 10,959,887 B2 | 3/2021 | Lenser et al. | |
| 10,966,876 B2 | 4/2021 | Lenser et al. | |
| 11,071,654 B2 | 7/2021 | Lenser et al. | |

(Continued)

*Primary Examiner* — Michael N Orlando
*Assistant Examiner* — Abhishek A Patwardhan
(74) *Attorney, Agent, or Firm* — Eversheds Sutherland (US) LLP

(57) ABSTRACT

Methods and apparatus for producing absorbent articles having a pocket, and absorbent articles having a pocket, are provided. The methods and apparatus include the continuous provision of nonwoven material and elastic strands, and the continuous bonding of elastic strands to nonwoven material, so as to continuously produce absorbent articles. The methods and apparatus further include a cut-and-turn wheel for accepting a continuous sheet of patch material, cutting patches, rotating the patches, and applying the patches to an absorbent article.

17 Claims, 15 Drawing Sheets

(56) References Cited

U.S. PATENT DOCUMENTS

| | | |
|---|---|---|
| 11,083,633 B2 | 8/2021 | Lenser et al. |
| 11,266,543 B2 | 3/2022 | Lenser et al. |
| 11,382,798 B2 | 7/2022 | Lenser et al. |
| 11,617,687 B2 | 4/2023 | Lenser et al. |
| 11,642,250 B2 | 5/2023 | Lenser et al. |
| 11,801,169 B2 | 10/2023 | McCormick et al. |
| 11,877,914 B2 | 1/2024 | Lenser et al. |
| 2003/0010423 A1* | 1/2003 | Nakakado ......... A61F 13/15593 156/229 |
| 2006/0184149 A1* | 8/2006 | Kasai ................ A61F 13/15658 604/367 |
| 2008/0312625 A1* | 12/2008 | Hundorf ............ A61F 13/5323 428/317.1 |
| 2012/0071852 A1* | 3/2012 | Tsang ................... A61F 13/496 156/179 |
| 2012/0077660 A1* | 3/2012 | Nakamura ............. B65H 37/04 493/374 |
| 2013/0012899 A1* | 1/2013 | Fenske .................... B32B 5/022 156/187 |
| 2013/0072887 A1* | 3/2013 | LaVon .............. A61F 13/49009 604/386 |
| 2014/0041783 A1* | 2/2014 | Nakano ............. A61F 13/15609 156/60 |
| 2015/0050462 A1* | 2/2015 | Schroer, Jr. ....... A61F 13/15658 428/188 |
| 2020/0375807 A1 | 12/2020 | Schneider et al. |
| 2020/0375815 A1 | 12/2020 | Raycheck et al. |
| 2021/0128366 A1 | 5/2021 | Schneider et al. |
| 2021/0128369 A1 | 5/2021 | Raycheck et al. |
| 2021/0346211 A1 | 11/2021 | Kilbacak et al. |
| 2021/0346213 A1 | 11/2021 | Kilbacak et al. |
| 2022/0106714 A1 | 4/2022 | Schneider et al. |
| 2024/0033132 A1 | 2/2024 | Lenser et al. |
| 2024/0050285 A1 | 2/2024 | Raycheck et al. |

\* cited by examiner

METHODS AND APPARATUS FOR MAKING ABSORBENT ARTICLES HAVING A POCKET AND ABSORBENT ARTICLES

FIELD OF THE DISCLOSURE

This disclosure relates generally to absorbent articles and, in particular, relates to methods and apparatus for making absorbent articles having a pocket for enhancing liquids and solids retention within the absorbent article.

BACKGROUND

Absorbent articles such as diapers are characterized by their ability to collect and retain solids and fluids. This collection and retention is usually accomplished by a liquid-permeable inner layer that contacts a user, a liquid impermeable outer layer that is exposed to the environment, and an absorbent core that collects liquids. However, if the amount of solids and/or liquids exceeds the liquid storage capacity of the absorbent core, liquids may leak. It is therefore desirable for the absorbent article to have as much liquids and solids retention as possible. However, simply increasing the size of the absorbent article and/or the size of the absorbent core may not be desirable and may increase the cost of the absorbent article for a many users.

There remains a need to increase the liquids and solids retention within the diaper at a relatively low cost.

BRIEF DESCRIPTION OF THE DRAWINGS

The detailed description is set forth with reference to the accompanying drawings. The use of the same reference numerals may indicate similar to identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Figure 1:
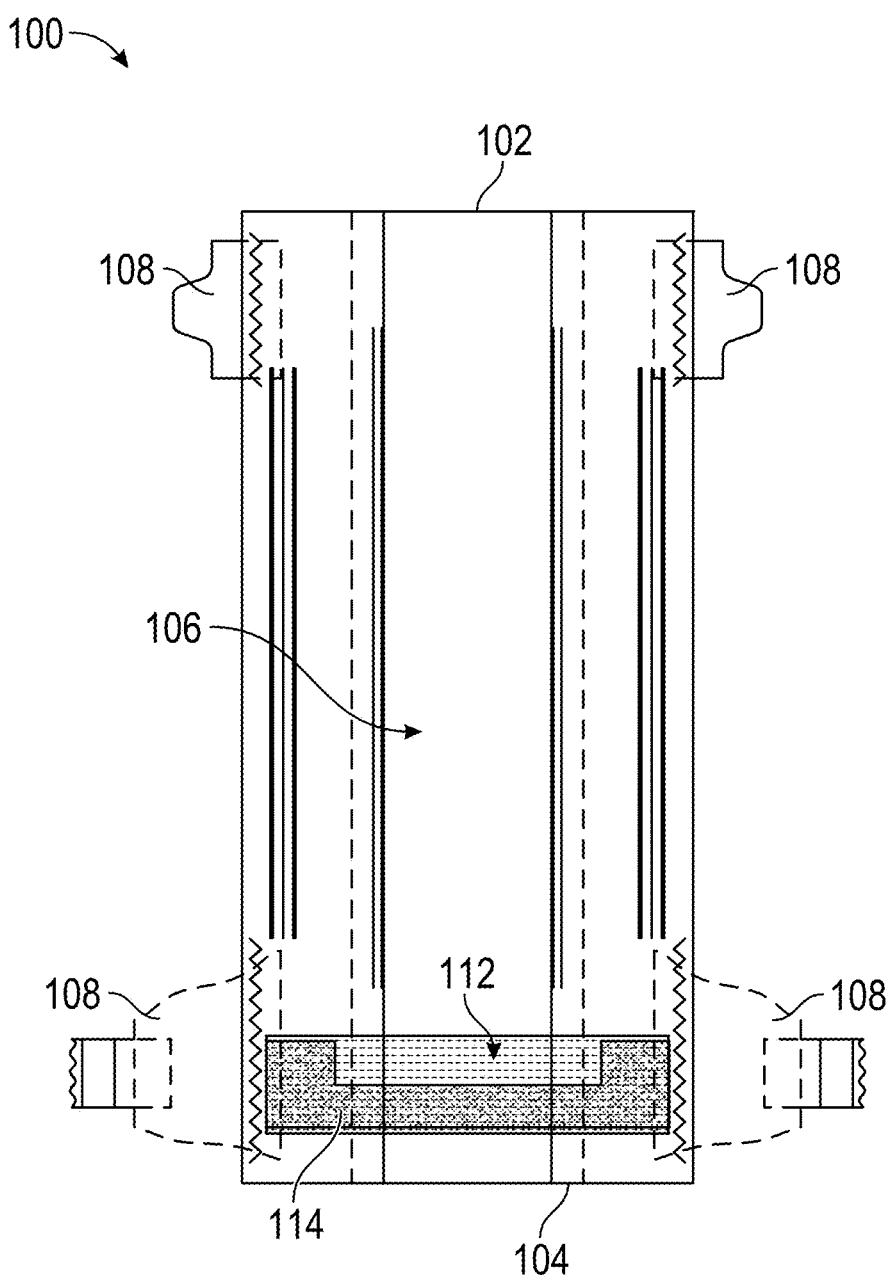
FIG. 1 depicts an unfolded absorbent article having a pocket in accordance with an embodiment of the disclosure in plan view.

Methods for producing absorbent articles having a pocket are provided herein, the methods including producing a patch and adhering the patch to an absorbent article. In particular, the methods include continuously accepting sheets of nonwoven material and strands of elastic material, forming an elastic nonwoven in-line, cutting the elastic nonwoven into discrete patches, and attaching a patch to an absorbent article. In some cases, the patch may be formed from one or more pieces of nonwoven material and the elastic strands may be bonded via ultrasonic bonding, thermomechanical bonding, or glue.

Also provided herein are apparatuses for forming absorbent articles having a pocket, the apparatuses including a patch forming module and an apparatus for applying a patch to an absorbent article. In particular, the patch forming module produces a continuous sheet of patch material that is glued, cut, rotated, and adhered to an absorbent article. In some cases, the apparatus may include components configured to align one or more sheets of nonwoven material, sometimes after cutting the nonwoven material, and bonding a plurality of elastic strands to and/or between sheets of nonwoven material.

Also provided herein are absorbent articles having a pocket configured to enhance the absorbent article's ability to retain solids and liquids therein. The pocket may have one or more sheets of nonwoven material with a plurality of elastic strands bonded on and/or between the nonwoven sheets.

Throughout this disclosure, various aspects are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

As used herein, the term "about" with reference to dimensions refers to the dimension plus or minus 10%.

Methods for Producing Absorbent Articles

Methods for producing absorbent articles having a pocket are provided herein. In some aspects, the methods include producing a patch, the patch including at least one nonwoven layer and a plurality of elastic strands bonded to the at least one nonwoven layer, and adhering the patch to an absorbent article to form a pocket.

As used herein, "absorbent article" refers to articles configured for use by a user for the relatively hygienic collection of solid and liquid waste. In some embodiments, the absorbent article is a diaper, such as a diaper configured to be worn by an infant, a diaper configured to be worn by a small child, a diaper configured to be worn by an adult, or any other diaper.

As used herein, a "patch" refers to an elastic piece of fabric generally including one or more pieces of nonwoven material that has been bonded to a plurality of elastic strands in a way that makes the nonwoven material stretch and contract.

Producing the Patch

In some embodiments, producing the patch includes providing at least one continuous sheet of nonwoven material in a machine direction (MD). As used herein, "providing" may refer to any means by which the at least one continuous sheet of nonwoven material is acquired or otherwise supplied for use in the method. For example, the at least one continuous sheet of nonwoven material may be acquired from a producer or manufacturer of such material and provided on, for example, a spool that is unwound as the at least one continuous sheet of nonwoven material is consumed in the method. As another example, a nonwoven manufacturing process may be adopted for producing the continuous sheet of nonwoven material immediately preceding and proximal to the methods described herein. Any suitable means for acquiring, supplying, or providing the at least one continuous sheet of nonwoven material is contemplated by "providing" the at least one continuous sheet of nonwoven material.

As used herein, "machine direction" or "MD" refers to the direction in which the apparatus on which the method is performed moves component materials during each step in the process. For example, a conveyor belt configured to transport materials inherently moves in the "machine direction." In contrast, the "cross-direction" or "CD" refers to the direction orthogonal to the machine direction. For example, a cutting apparatus configured to cut materials on a conveyor belt at regular intervals may move in the CD.

In some embodiments, the producing the patch further includes providing a plurality of elastic strands in the MD and positioning the plurality of elastic strands on the at least one continuous sheet of nonwoven material. The plurality of elastic strands may be provided on a single spool and passed through a comb, sieve, or rake in order to separate and align the strands. The plurality of elastic strands may be provided on a plurality of spools such that one spool provides one elastic strand, and each of the plurality of spools may be positioned proximal to one another so that the plurality of elastic strands are aligned according to the desired elastic strand profile. The plurality of elastic strands may be manufactured by a method performed proximal to the methods described herein instead of being provided on a spool. Any suitable means for providing the plurality of elastic strands is contemplated.

As used herein, "positioning" the plurality of elastic strands on the at least one continuous sheet of nonwoven material, or positioning on or between other structures as described herein, refers to moving the plurality of elastic strands and the at least one continuous sheet of nonwoven material in the same direction, i.e., the machine direction, while bringing the elastic strands and nonwoven material into close proximity and/or in contact with one another. For example, the elastic strands and nonwoven material may be provided to the method under tension, such as from spools, and they may be passed over an alignment wheel or other structure such that the elastic strands are in contact with the nonwoven material and move concurrently with one another.

In some embodiments, producing the patch includes bonding the plurality of elastic strands to the at least one continuous sheet of nonwoven material to form a continuous sheet of patch material. In other words, the patch is characterized by elastic strands bonded to and/or between sheets of nonwoven material. By bonding the plurality of elastic strands continuously, a single, uninterrupted sheet of "patch material" is produced, which may subsequently be cut into a plurality of patches.

In some embodiments, bonding the plurality of elastic strands to the at least one continuous sheet of nonwoven material may include ultrasonic bonding, such as by passing the elastic strands and nonwoven material over an anvil and pressing an ultrasonic horn against the material, thereby forming one or more ultrasonic bonds that joins the layers together. In some embodiments, the bonds formed seal only the nonwoven material, thereby entrapping the elastic strands between layers of nonwoven material. In other embodiments, the elastic strands are directly bonded by the ultrasonic horn and anvil. In some embodiments, the anvil has a plurality of protrusions that are engaged by the ultrasonic horn to form the ultrasonic bonds. In other embodiments, the anvil is relatively flat, and the ultrasonic horn has a plurality of protrusions for forming the ultrasonic bonds.

In some embodiments, bonding the plurality of elastic strands to the at least one continuous sheet of nonwoven material may include thermomechanical bonding, such as by passing the elastic strands and nonwoven material over an anvil and pressing a heated bonding wheel against the material, thereby forming one or more thermomechanical bonds that joins the layers together. In some embodiments, the bonds formed seal only the nonwoven material, thereby entrapping the elastic strands between layers of nonwoven material. In other embodiments, the elastic strands are directly bonded by the heated bonding wheel and the anvil. In some embodiments, the anvil has a plurality of protrusions that are engaged by the heated bonding wheel to form the thermomechanical bonds. In other embodiments, the anvil is relatively flat, and the heated bonding wheel has a plurality of protrusions for forming the thermomechanical bonds.

In some embodiments, bonding the plurality of elastic strands to the at least one continuous sheet of nonwoven material may include glue, such as by passing the at least one continuous sheet of nonwoven material and/or the plurality of elastic strands over a glue applicator before passing the elastic strands and nonwoven material through a pair of pressing rolls that press the layers together, effecting adhesion with the glue that has been applied by the glue applicator.

In some embodiments, producing the patch further comprises cutting the continuous sheet of patch material at regular intervals in the cross-direction to produce a plurality of patches.

In some embodiments, exactly one continuous sheet of nonwoven material is provided when producing the patch. In some embodiments, the plurality of elastic strands are positioned on the continuous sheet of nonwoven material and the continuous sheet of nonwoven material is folded, such as by a folding chute. The folding may be in the CD such that a first longitudinal edge of the continuous sheet of nonwoven material is folded towards the middle of the nonwoven material and a second longitudinal edge of the continuous sheet of nonwoven material is folded towards the middle of the nonwoven material. In other words, the first and second longitudinal edges of the nonwoven material may each be folded towards one another such that the longitudinal edges overlap, thereby forming a seam running in the MD. Furthermore, the first and second longitudinal edges of the nonwoven material may be folded over and on top of the plurality of elastic strands such that the each elastic strand is positioned between an upper portion of the continuous nonwoven material and a lower portion of the continuous nonwoven material.

In some embodiments, producing the patch includes bonding the seam formed by folding the first and second longitudinal edges of the nonwoven material such as by bonding the first longitudinal edge to the second longitudinal edge and/or bonding the first and second longitudinal edges to the lower portion of the nonwoven material. In some embodiments, producing the patch includes bonding the plurality of elastic strands to the folded continuous sheet of nonwoven material such that each elastic strand is bonded between the upper portion of the continuous nonwoven material and the lower portion of the continuous nonwoven material. In some embodiments, bonding the seam and bonding the plurality of elastic strands involves the same bonding process, i.e., a bond may be formed that joins the first and second longitudinal edges, i.e., the "upper portion" of the continuous nonwoven material, and the lower portion of the continuous nonwoven material, thereby bonding the seam and the elastic strands with the same "bonds." In some embodiments, bonding the seam and/or the plurality of elastic strands is performed using ultrasonic bonding, thermomechanical bonding, and/or glue, as described previously. Upon bonding the seam and the plurality of elastic strands, a continuous sheet of patch material results that may then be cut to produce a plurality of patches.

In some embodiments, first and second continuous sheets of nonwoven material are provided when producing the patch. As described previously, the first and second continuous sheets of nonwoven material may be provided in a number of ways. In some embodiments, a single continuous sheet of nonwoven material is provided and is cut into first and second continuous sheets of nonwoven material such as by a cutting or slitting apparatus. In some embodiments, the first and second continuous sheets of nonwoven material are substantially identical in size, shape, and in material. In some embodiments, the first and second continuous sheets of nonwoven material differ in size, shape, or material depending on the needs of the application.

In some embodiments, the plurality of elastic strands are positioned between the first and second continuous sheets of nonwoven material such that the first and second continuous sheets of nonwoven material substantially overlap one another with the plurality of elastic strands disposed in between. The plurality of elastic strands may then be bonded between the first and second continuous sheets of nonwoven material, such as through an ultrasonic bonding process, thermomechanical bonding process, or a gluing process, as described previously.

After elastic strand bonding, the first and second continuous sheets of nonwoven material may then be folded. In some embodiments, a first longitudinal edge of the first continuous sheet of nonwoven material and a first longitudinal edge of the second continuous sheet of nonwoven material may be concurrently folded to form a first folded edge. The first folded edge may then be bonded, thereby securing the first folded edge to one or both of the first or second continuous sheets of nonwoven material. Bonding the first folded edge may be performed by, for example, ultrasonic bonding, thermomechanical bonding, or gluing, as described previously.

In some embodiments, simultaneous or subsequent to folding the first longitudinal edges, a second longitudinal edge of the first continuous sheet of nonwoven material and a second longitudinal edge of the second continuous sheet of nonwoven material may be concurrently folded for form a second folded edge. The second folded edge may then be bonded, thereby securing the second folded edge to one or both of the first or second continuous sheets of nonwoven material. Bonding the second folded edge may be performed by, for example, ultrasonic bonding, thermomechanical bonding, or gluing, as described previously.

In some embodiments, the first and second edges may be folded in the same direction, i.e., so that each folded edge is positioned adjacent to the same continuous sheet of nonwoven material. In some embodiments, the first and second folded edges may be folded in different directions, i.e., so that one is positioned adjacent to the first continuous sheet of nonwoven material and the other is positioned adjacent to the second continuous sheet of nonwoven material. In some embodiments, "bonding" the first and second folded edges may involve forming one or more bonds through the entire stack of nonwoven layers which may include, for example, the first longitudinal edge of the first continuous sheet of nonwoven material, the first longitudinal edge of the second continuous sheet of nonwoven material, a portion of the first continuous sheet of nonwoven material, and a portion of the second continuous sheet of nonwoven material. Upon bonding the first and second folded edges and the plurality of elastic strands, a continuous sheet of patch material results that may then be cut to produce a plurality of patches.

As used herein, a "longitudinal edge" refers to the outermost portion of the nonwoven material in the cross-direction. The longitudinal edge may include a small portion of the nonwoven material, such as approximately 5% of the nonwoven material. In other words, a nonwoven material having a width of, for example, 100 mm may have a first longitudinal edge extending approximately 5 mm from a first outermost edge of the nonwoven material, approximately 90 mm of uninterrupted nonwoven material, and then a second longitudinal edge extending approximately 5 mm from a second outermost edge of the nonwoven material located opposite from the first outermost edge in the cross-direction. The longitudinal edges may have other dimensions, such as from about 1% to about 15% of the width of the nonwoven material.

In some embodiments, the bonding of the elastic strands to the nonwoven material may effectively involve bonding the nonwoven material together with the elastic strands entrapped therebetween. In other words, and especially with ultrasonic or thermomechanical bonding, "bonding" the plurality of elastic strands may not involve bonding the strands directly, but may instead involve forming ultrasonic or thermomechanical bonds immediately adjacent to the elastic strands in a way that entraps the elastic strands and prevents the elastic strands from moving laterally, longitudinally, or both. Some bonds are effective only to prevent elastic strands from moving laterally, i.e., in the CD, but otherwise allow the strands to move longitudinally. These bonds are separated by a distance greater than the width of the elastic strand. Other bonds are effective to prevent elastic strands from moving laterally or longitudinally such as by "squeezing" the elastic strand. These bonds are separated by a distance lesser than the width of the elastic strand and are normally formed while the elastic strands are tensioned.

In some embodiments, bonding the plurality of elastic strands include forming a plurality of bond pairs, each bond pair including a first bond a second bond separated by a distance configured to entrap one of the elastic strands therebetween in a tensioned state. For example, an untensioned elastic strand may have a first width but this width may drop by 5-50% upon tensioning or stretching the elastic strand. An elastic strand may have an untensioned width of mm, for example, but a tensioned width of mm. Thus, the bond pair described herein may be separated by a distance corresponding to the tensioned width, such as the exemplary mm. Upon allowing the elastic strand to retract to its untensioned state and untensioned width, the bond pair entraps the elastic strand effectively preventing the elastic strand from moving without directly forming a bond through the elastic strand itself.

In some embodiments, a portion of the plurality of bond pairs do not have an elastic strand entrapped therebetween. In other words, the bonding process may be performed on an apparatus configured to form a number of bonding pairs that exceeds the number of elastic strands. In these embodiments, the elastic strand is configured to be entrapped by at least one of the bonding pairs in a given row of bonds.

In some embodiments, bonding the plurality of elastic strands includes forming a plurality of non-bonding pairs, each non-bonding pair including a first bond and a second bond separated by a distance configured to permit an elastic strand positioned therebetween to tension and relax without restriction. Thus, by precisely positioning bonding pairs and non-bonding pairs, the elasticity of the resulting patch may be tuned.

In some embodiments, the plurality of elastic strands are continuously bonded to the at least one continuous sheet of nonwoven material. In other words, as the continuous sheet of nonwoven material is supplied to the method, and as the plurality of elastic strands are continuously supplied to the method, the nonwoven material and elastic strands are continuously positioned as described above and continuously bonded. The result is a continuous sheet of patch material that is substantially uniform in bond density, elastic strand density and position, and elasticity. Such continuous bonding may be performed by, for example, a bonding wheel that continuously rotates coincident to the passage of the nonwoven material and elastic strands, enabling the continuous formation of bonds.

In some embodiments, the plurality of elastic strands are intermittently bonded to the at least one continuous sheet of nonwoven material. In other words, as the continuous sheet of nonwoven material is supplied to the method, and as the plurality of elastic strands are continuously supplied to the method, the nonwoven material and elastic strands are continuously positioned as described above but bonded at intermittent intervals. For example, a period of bonding may occur to form a bonded portion of material followed by a period of non-bonding that forms a portion of non-bonded material before resuming bonding. After cutting the continuous sheet of nonwoven material to form the plurality of patches, the intermittent bonding process may result in a patch having a first lateral edge without bonds, a central portion with bonds, and a second edge without bonds. As used herein, a "lateral edge" is an edge along the CD that is orthogonal to the MD and to the longitudinal edges. In a continuous sheet of material, there may be no "lateral edge" until the material is cut.

Adhering the Patch to the Absorbent Article

After producing a patch or a continuous sheet of patch material, the patch must then be adhered to an absorbent article in order to produce the absorbent article having a pocket.

In some embodiments, adhering the patch to the absorbent article include providing a plurality of absorbent articles in a machine direction (MD). For example, the absorbent articles may be supplied via a conveyor. The absorbent articles may be a plurality of discrete absorbent articles or may be a continuous sheet of connected absorbent articles that are intended to be cut and separated after patch adhesion. The absorbent articles may be acquired by a producer or manufacturer of such articles and supplied to the method through any suitable means, such as by unrolling a continuous sheet of absorbent articles from a spool. The absorbent articles may be produced by a production method performed immediately adjacent to the patch formation and adhesion processes.

In some embodiments, adhering the patch to the absorbent article includes providing a continuous sheet of patch material. The continuous sheet of patch material may be produced as described previously and may include at least one continuous sheet of nonwoven material and a plurality of elastic strands bonded thereto via one or more of ultrasonic bonding, thermomechanical bonding, or glue.

Upon providing the continuous sheet of patch material, the method may include applying glue to the continuous sheet of patch material. The glue may be ultimately intended to enable adhesion of the patch to the absorbent article. It may be simpler to apply glue to the continuous sheet of patch material in a continuous glue application process rather than applying glue after cutting the continuous sheet of patch material into a plurality of patches.

In some embodiments, applying glue to the continuous sheet of patch material may include moving the continuous sheet of patch material in the machine direction across a glue applicator. In some embodiments, the glue applicator is configured to apply glue continuously across a first portion of the continuous sheet of patch material and to apply glue intermittently across a second portion of the continuous sheet of patch material. The first portion and second portion may be disposed adjacent to one another in the cross-direction. By applying glue continuously in a first portion and intermittently in a second portion, a glue pattern forms including an adhering region and a non-adhering region, the non-adhering region partially bounded by the adhering region. In this way, a glue pattern results that enables the formation of a pocket accessible via the non-adhering portion of the glue pattern when the patch is applied to the absorbent article. For example, in some embodiments, the glue is applied to the continuous sheet of patch material in a pattern that, when the continuous sheet of patch material is cut into a plurality of patches, results in a "C"-shaped pattern on each patch.

In some embodiments, after applying glue, the continuous sheet of patch material may be supplied to an alignment wheel. The alignment wheel may be configured to pick up or otherwise "grab" the continuous sheet of patch material such as through the use of a vacuum, which will be described in greater detail in the description of the apparatus. In some embodiments, after supplying the continuous sheet of patch material to the alignment wheel, the continuous sheet of patch material is cut at regular intervals in the cross-direction to produce a plurality of patches. For example, the continuous sheet of patch material may be passed next to a cutting wheel that is disposed adjacent to the alignment wheel, the cutting wheel having a plurality of blades spaced at a distance and rotated at a speed such that the continuous sheet of patch material is cut at desired locations effective to produce the plurality of patches.

After cutting the continuous sheet of patch material into a plurality of patches, the patches are rotated 90°. The alignment wheel may be equipped with rotatable pucks, each puck configured to hold a patch such that each patch may be rotated by the puck after cutting. Because of the continuous nature of the patch production process, the elasticity of the patch is initially in the machine direction. However, it is desirable to apply the patch to the absorbent article such that the elasticity is in the cross-direction. Thus, the method may include rotating the patch 90°.

After rotating the patch 90°, the method may include aligning the patch with one of the absorbent articles. This alignment may be performed by synchronous movement of the alignment wheel and the absorbent article provision means. If, for example, the plurality of absorbent articles are provided via a conveyor, the conveyor and the alignment wheel may be moving at relative speeds that result in alignment of a patch with an absorbent article. As will be explained in greater detail, the speed of the alignment wheel may be equal to or different from the speed of the conveyor provided the patch is in the desired position relative to the absorbent article when adhered. In some embodiments, aligning the patch with the absorbent article includes aligning the patch with an inner surface of the absorbent article, the inner surface corresponding to the surface intended to contact a user when the absorbent article is worn by the user. In this way, the patch may form a pocket configured to improve the liquids and solids retention of the absorbent article. In some embodiments, aligning the patch with the absorbent article includes aligning the "C"-shaped glue pattern on the patch such that the glue pattern enables the formation of a pocket when the patch is adhered to the absorbent article.

In some embodiments, once the patch has been rotated 900 and aligned with an absorbent article, the patch is pressed against the absorbent article. The pressing may be effective to induce adhesion of the patch to the absorbent article via the glue that was applied to the patch. The pressing may be done by any suitable means, including a press that actuates the patch against the absorbent article or vice versa, an oval or oblong shaped wheel configured to intermittently apply force to an absorbent article when the patch is aligned, or another suitable pressing means.

In some embodiments, the continuous sheet of patch material is supplied to the alignment wheel at a first speed, the alignment wheel rotates at a second speed, and the plurality of absorbent articles are supplied at a third speed. It sometimes desirable to tension or stretch the elastics within the patch upon adhering the patch to the absorbent article depending on the characteristics of the desired final product. By manipulating the relative speeds of the continuous sheet of patch material, the alignment wheel, and the plurality of absorbent articles, the degree of tension experienced by the patch as it is applied to the absorbent article can be tuned.

In some embodiments, the first speed is lower than the second speed, and the second speed is equal to the third speed. In other words, the speed at which the continuous sheet of patch material is supplied to the alignment wheel is lower than the speed of the alignment wheel and the speed of the alignment wheel is equal to the speed at which the plurality of absorbent articles are provided. This results in an elongation or tensioning of the continuous sheet of patch material as it is collected by the alignment wheel and prior to cutting the continuous sheet of patch material. After rotation, each patch will be tensioned in the cross-direction as it is adhered to the absorbent article.

In some embodiments, the first speed is equal to the second speed and the second speed is lower than the third speed. In other words, the speed at which the continuous sheet of patch material is supplied to the alignment wheel is equal than the speed of the alignment wheel and the speed of the alignment wheel is lower than the speed at which the plurality of absorbent articles are provided. This results in an elongation of each patch as it is applied to the absorbent article, which is a stretching in a direction orthogonal to the elastic strands themselves.

Apparatuses for Producing Absorbent Articles

Apparatuses for producing absorbent articles are also provided herein. In some aspects, the apparatus includes a patch-forming module and a module for the gluing, cutting, turning, and adhesion of the patch to an absorbent article.

Patch Forming Modules

In some embodiments, the apparatus includes a patch-forming module configured to form a continuous sheet of patch material that comprises at least one nonwoven layer and a plurality of elastic strands bonded to the at least one nonwoven layer.

The patch-forming module may be configured to form a patch from a single continuous sheet of nonwoven material. In some embodiments, the patch-forming module may include a folding chute configured to receive a continuous sheet of nonwoven material in a machine direction and a plurality of elastic strands in the machine direction. The folding chute may be configured to fold a first longitudinal edge of the continuous sheet of nonwoven material in a cross-direction and a second longitudinal edge of the continuous sheet of nonwoven material in the cross-direction such that the first longitudinal edge and the second longitudinal edge enclose the plurality of elastic strands and overlap one another so that a seam is formed running in the machine direction. This folding chute may be effective for receiving and folding the nonwoven material when there is exactly one sheet of nonwoven material.

After the folding chute, the apparatus may include an ultrasonic bonding unit, a thermomechanical bonding unit, or a gluing unit.

In some embodiments, the ultrasonic bonding unit includes a rotating anvil configured to receive the folded continuous sheet of nonwoven material and an ultrasonic horn configured to intermittently press the folded continuous sheet of nonwoven material against the rotating anvil in order to form ultrasonic bonds. These ultrasonic bonds may bond the plurality of elastic strands within the folded continuous sheet of nonwoven material, and may also bond the seam, thereby forming the continuous sheet of patch material.

The rotating anvil in the ultrasonic bonding unit may include a plurality of rows of protrusions extending across a surface of the rotating anvil, each row of protrusions extending from a first edge of the rotating anvil to a second edge of the rotating anvil in a cross-direction. In some embodiments, each row of protrusions extends across the surface of the rotating anvil in a "zig-zag" pattern such that every circumferential position on the rotating anvil includes at least one protrusion from one of the plurality of rows of protrusions. In other words, the ultrasonic horn may be smooth and extending uninterrupted in the cross-direction. By ensuring that every circumferential position on the anvil has at least one protrusion, the ultrasonic horn may have at least one point of contact with the rotating anvil at all times, reducing the complexity of the apparatus overall. Furthermore, adjacent protrusions on the rotating anvil may be separated by a distance configured to entrap an elastic strand bonded therebetween. There may be a number of protrusions that form bonds without any elastic strand entrapped. By ensuring the distance between adjacent protrusions is separated by a distance configured to entrap an elastic strand, the elastic strand will be entrapped by at least one pair of adjacent protrusions. When the folded continuous sheet of nonwoven material passes in between the rotating anvil and the ultrasonic horn, the ultrasonic horn will press against the material and form bonds corresponding to the protrusions.

The rotating anvil in the ultrasonic bonding unit may include a plurality of rows of protrusions extending across a surface of the rotating anvil, each row of protrusions extending from a first edge of the rotating anvil to a second edge of the rotating anvil in a cross direction. In some embodiments, each row of protrusions extends across the surface of the rotating anvil in a direction orthogonal to a circumferential axis of the rotating anvil. In other words, the rotating anvil may have a substantially flat surface and may rotate in a machine direction, and each row of protrusions may extend across the substantially flat surface from a first edge to a second edge in the cross-direction. In some embodiments, each row of protrusions includes a plurality of bond protrusion pairs each having a first protrusion and a second protrusion separated by a distance configured to entrap an elastic strand therebetween in a tensioned state. Each row of protrusions may further include a plurality of non-bonding protrusion pairs each having a first protrusion and a second protrusion separated by a distance configured to permit an elastic strand positioned therebetween to tension and relax without restriction. When the folded continuous sheet of nonwoven material passes in between the rotating anvil and the ultrasonic horn, the ultrasonic horn will press against the material and form bonds corresponding to the protrusions.

In some embodiments, the thermomechanical bonding unit includes a rotating anvil configured to receive the folded continuous sheet of nonwoven material and a heated roll positioned adjacent to and in contact with the rotating anvil. Together, the rotating anvil and heated roll may be configured to thermomechanically seal the plurality of elastic strands within the folded continuous sheet of nonwoven material, and to thermomechanically seal the seam, thereby forming the continuous sheet of patch material.

The rotating anvil in the thermomechanical bonding unit may include a plurality of rows of protrusions extending across a surface of the rotating anvil, each row of protrusions extending from a first edge of the rotating anvil to a second edge of the rotating anvil in a cross direction. In some embodiments, each row of protrusions extends across the surface of the rotating anvil in a direction orthogonal to a circumferential axis of the rotating anvil. In other words, the rotating anvil may have a substantially flat surface and may rotate in a machine direction, and each row of protrusions may extend across the substantially flat surface from a first edge to a second edge in the cross-direction. In some embodiments, each row of protrusions includes a plurality of bond protrusion pairs each having a first protrusion and a second protrusion separated by a distance configured to entrap an elastic strand therebetween in a tensioned state. Each row of protrusions may further include a plurality of non-bonding protrusion pairs each having a first protrusion and a second protrusion separated by a distance configured to permit an elastic strand positioned therebetween to tension and relax without restriction. When the folded continuous sheet of nonwoven material passes in between the rotating anvil and the heated wheel, the heated wheel will press against the material and form bonds corresponding to the protrusions.

In some embodiments, the gluing unit may include a first glue applicator configured to apply glue to the plurality of elastic strands before entering the folding chute and a second glue applicator configured to apply glue to the first longitudinal edge and the second longitudinal edge of the continuous sheet of nonwoven material before entering the folding chute. After exiting the folding chute, the folded continuous sheet of nonwoven material may pass through a pair of pressing rolls configured to effectuate adhesion of the plurality of elastic strands within the folded continuous sheet of nonwoven material, and to effectuate adhesion of the seam. The pair of pressing rolls may be configured to have a nominal gap between the pair of pressing rolls so that the folded continuous sheet of nonwoven material is pressed together, ensuring the glue applied by the first and second glue applicators effectively adheres the materials together.

The patch-forming module may be configured to form a patch from two continuous sheets of nonwoven material. In some embodiments, the patch-forming module may include a slitter configured to accept a continuous source of nonwoven material and slit the continuous source of nonwoven material into a first continuous sheet of nonwoven material and a second continuous sheet of nonwoven material. After the slitter, the patch-forming module may include a first steering guide configured to accept the first continuous sheet of nonwoven material and a second steering guide configured to accept the second continuous sheet of nonwoven material. The first and second steering guides may be further configured to align the first and second continuous sheets of nonwoven material with one another, i.e., may position one continuous sheet of nonwoven material "above" or otherwise in-line with the other continuous sheet of nonwoven material so that the continuous sheets of nonwoven material may be easily pressed together in a subsequent step.

In some embodiments, the patch-forming module further includes a third steering guide configured to accept a plurality of elastic strands and align the plurality of elastic strands between the first and second continuous sheets of nonwoven material. Thus, the first, second, and third steering guides effectively position the first continuous sheet of nonwoven material, the plurality of elastic strands, and the second continuous sheet of nonwoven material in-line with one another.

After the first continuous sheet of nonwoven material, the plurality of elastic strands, and the second continuous sheet of nonwoven material are effectively steered by the steering guides so that they are in-line with one another, they may then be bonded, such as by an ultrasonic bonding unit, a thermomechanical bonding unit, or a gluing unit. These bonding units may be the same or substantially similar to those described previously.

In some embodiments, the ultrasonic bonding unit includes a rotating anvil configured to receive the first continuous sheet of nonwoven material, the plurality of elastic strands, and the second continuous sheet of nonwoven material, and an ultrasonic horn configured to intermittently press the first and second continuous sheets of nonwoven material, with elastic strands disposed in between, against the rotating anvil in order to form ultrasonic bonds. These ultrasonic bonds may bond the plurality of elastic strands within the first and second continuous sheets of nonwoven material.

In some embodiments, the thermomechanical bonding unit includes a rotating anvil configured to receive the first continuous sheet of nonwoven material, the plurality of elastic strands, and the second continuous sheet of nonwoven material, and a heated roll positioned adjacent to and in contact with the rotating anvil. Together, the rotating anvil and heated roll may be configured to thermomechanically seal the plurality of elastic strands within the first and second continuous sheets of nonwoven material.

After either ultrasonically bonding or thermomechanically bonding the first continuous sheet of nonwoven material, the plurality of elastic strands, and the second continuous sheet of nonwoven material together, a continuous sheet of bonded elastic nonwoven material is formed. However, the longitudinal edges of the first and second continuous sheets of nonwoven material may remain loose. Thus, the continuous sheet of bonded elastic nonwoven material may next pass through a folding chute configured to receive the continuous sheet of bonded elastic nonwoven material in a machine direction (MD), wherein the folding chute is configured to fold a first longitudinal edge of the continuous sheet of bonded elastic nonwoven material in a cross-direction and a second longitudinal edge of the continuous sheet of bonded elastic nonwoven material in the cross-direction. The folded first and second longitudinal edges may next be bonded using, for example, a thermomechanical sealing unit comprising a rotating anvil and heated roll, as described herein. After bonding the plurality of elastic strands within the continuous sheets of nonwoven material and after folding and bonding the longitudinal edges, the continuous sheet of patch material results.

The rotating anvil used for either ultrasonic bonding or thermomechanical bonding may have a plurality of protrusions for forming the bonds, as described previously.

In some embodiments, the gluing unit may include a first glue applicator configured to apply glue to the plurality of elastic strands and a first pair of pressing rolls configured to press and to effectuate adhesion of the first continuous sheet of nonwoven material, the plurality of elastic strands, and the second continuous sheet of nonwoven material, thereby forming a continuous sheet of glued elastic nonwoven material. The gluing unit may then include a second glue applicator configured to apply glue to the first longitudinal edge and the second longitudinal edge of the continuous sheet of glued elastic nonwoven material. The continuous sheet of glued elastic nonwoven material may then enter a folding chute configured to fold a first longitudinal edge of the continuous sheet of bonded elastic nonwoven material in a cross-direction (CD) and a second longitudinal edge of the continuous sheet of bonded elastic nonwoven material in the CD. After exiting the folding chute, the folded continuous sheet of glued elastic nonwoven material may then pass through a second pair of pressing rolls configured to effectuate adhesion of the first and second folded longitudinal edges, thereby forming the continuous sheet of patch material. The first and second pairs of pressing rolls may be configured to have a nominal gap between the pairs of pressing rolls so that the material is pressed together, ensuring the glue applied by the first and second glue applicators effectively adheres the materials together. After gluing the plurality of elastic strands within the continuous sheets of nonwoven material and after folding and gluing the longitudinal edges, the continuous sheet of patch material results.

Apparatus for Attaching Patch to Absorbent Article

After the continuous sheet of patch material is formed by the patch-forming module, the apparatus includes a primary glue applicator configured to apply glue to the continuous sheet of patch material. The primary glue applicator may be configured to apply glue in a pattern including an adhering portion and a non-adhering portion, the non-adhering portion partially bounded by the adhering portion. In some embodiments, the primary glue applicator is configured to apply glue continuously across a first portion of the continuous sheet of patch material and to apply glue intermittently at regular intervals across a second portion of the continuous sheet of patch material, wherein the first portion is adjacent to the second portion in the cross-direction. In other words, after cutting the continuous sheet of patch material, the glue pattern applied by the primary glue applicator may have a "C"-shaped pattern.

The apparatus may next include a cut-and-turn wheel including a plurality of rotatable vacuum pucks configured to accept the continuous sheet of patch material. The rotatable vacuum pucks may "pick up" or otherwise accept and secure the continuous sheet of patch material on a side of the continuous sheet of patch material opposite to the glue pattern applied by the primary glue applicator.

In some embodiments, the apparatus includes a cutting wheel having a plurality of blades configured to rotate coincident to the cut-and-turn wheel. In other words, the number of blades and rotation speed of the cutting wheel is tuned so that the continuous sheet of patch material is cut at precisely the correct locations to produce the desired plurality of patches. This cutting rate is also tuned to the number and location of rotatable vacuum pucks so that each patch in the resulting plurality of patches is secured to one of the rotatable vacuum pucks.

After cutting, each rotatable vacuum puck may be configured to rotate 90°, thereby rotating the patch secured to the rotatable vacuum puck by 90°.

In some embodiments, the apparatus includes a conveyor configured to supply a plurality of absorbent articles. The conveyor may be configured such that each absorbent article is positioned adjacent to a patch after the patch has been rotated by the corresponding rotatable vacuum puck. A phased roll having an oval or oblong shape may be positioned adjacent to the conveyor at the point where the absorbent article is adjacent to the patch. The phased roll may have a major diameter and a minor diameter so that, when the phased roll rotates, periodic pressure is applied to the conveyor and the absorbent article that may be present. When a patch has been rotated by the rotatable vacuum puck and has been positioned by the cut-and-turn wheel, an absorbent article will be positioned adjacent to the patch by virtue of the synchronous speeds of the conveyor and the cut-and-turn wheel. Furthermore, the phased roll, by virtue of synchronous speed, will rotate its major diameter against the absorbent article, thereby applying sufficient pressure to effectuate adhesion of the patch to the absorbent article.

In some embodiments, the patch forms a pocket when adhered to the absorbent article by virtue of the glue pattern applied to the patch by the primary glue applicator, thereby forming an absorbent article having a pocket.

Absorbent Articles

Absorbent articles are also provided herein including pockets for improved liquids and solids retention when worn by a user.

In some embodiments, the absorbent article includes a patch adhered to the absorbent article. The patch may be adhered using a glue pattern including a non-adhesion region partially bound by an adhesion region so that a pocket is formed. In some embodiments, the glue pattern is a "C"-shaped glue pattern.

In some embodiments, the patch includes at least one piece of nonwoven material and a plurality of elastic strands bonded to the at least one piece of nonwoven material. The bonds may be ultrasonic bonds, ultrasonic bonds, or bonds formed using glue.

When the bonds are ultrasonic or thermomechanical bonds, the plurality of elastic strands may be bonded to the at least one piece of nonwoven material using a bond pattern including a plurality of rows of bonds extending from a first longitudinal edge of the patch to a second longitudinal edge of the patch, each row of bonds having a "zig-zag" pattern such that every lateral position on the patch includes at least one bond from one of the plurality of rows of bonds. Adjacent bonds in each row of bonds may be separated by a distance configured to entrap an elastic strand bonded therebetween. In some embodiments, only a portion of the bonds entrap an elastic strand.

The patch may include exactly one piece of nonwoven material that has been folded around the plurality of elastic strands and bonded at a seam using ultrasonic bonds, thermomechanical bonds, and/or glue. The patch may include a first piece of nonwoven material and a second piece of nonwoven material, and the plurality of elastic strands may be bonded between the first and second pieces of nonwoven material. The first and second pieces of nonwoven material may be bonded together at a first longitudinal edge and a second longitudinal edge using ultrasonic bonds, thermomechanical bonds, and/or glue.

In some embodiments, the patch is adhered to an inner surface of the absorbent article so that the patch is configured to contact a user when the absorbent article is worn. In some embodiments, the patch is positioned proximal to a first lateral edge of the absorbent article such that an opening formed by the glue pattern is facing a second lateral edge of the absorbent article.

Turning now to the Figures, FIG. 1 depicts an absorbent article 100, which is depicted as a diaper. Absorbent article 100 has a front waist edge 102, a back waist edge 104, crotch region 106, front fastening elements 108, and rear fastening elements 110. A pocket region 112 is formed by the adhesion of a patch 114 to the absorbent article 100.

Figure 2:
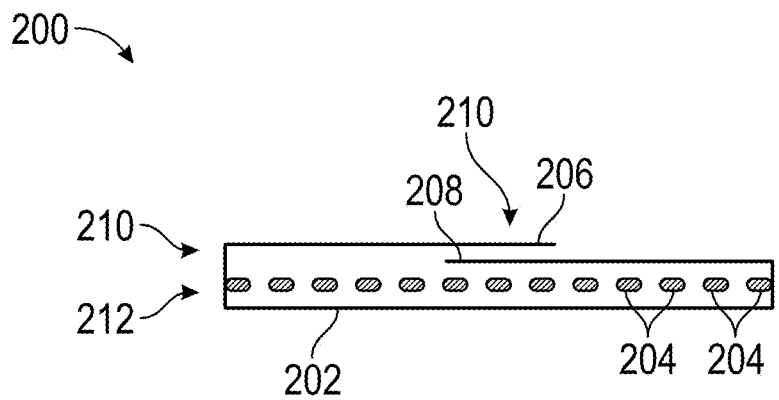
FIG. 2 depicts a schematic side view in cross-section of a patch in accordance with an embodiment of the disclosure.

FIG. 2 depicts a schematic side view in cross-section of a patch 200. The patch 200 includes a single piece of nonwoven fabric 202 that has been folded around a plurality of elastic strands 204. A first longitudinal edge 206 of the patch 200 overlaps a second longitudinal edge 208 to form a seam 210. The elastic strands 204 are disposed in between an upper portion 210 of the nonwoven fabric 202 and a lower portion 212 of the nonwoven fabric. The upper portion 210 and lower portion 212 of the nonwoven fabric are bonded together using bonds (not depicted in this Figure). Although first longitudinal edge 206 is depicted as lying "on top" of second longitudinal edge 208, this order may be reversed or may be a matter of perspective. In other words, the patch may be symmetrical such that the opposite side view in cross-section appears to depict the second longitudinal edge "on top" of the first longitudinal edge. The decision to depict one longitudinal edge above the other to the exclusion of other embodiments is in the interest of brevity only and is not intended to limit the invention. Furthermore, although the terms "upper portion" and "lower portion" are used to describe the relative positions of the nonwoven fabric relative to the elastic strands, it is to be understood that such relative positioning is not dependent on the patch's disposition in three-dimensional space. In other words, the "upper portion" remains opposed to the "lower portion" as depicted regardless of whether the "upper portion" is positionally above or "upper" relative to the lower portion.

Figure 3:
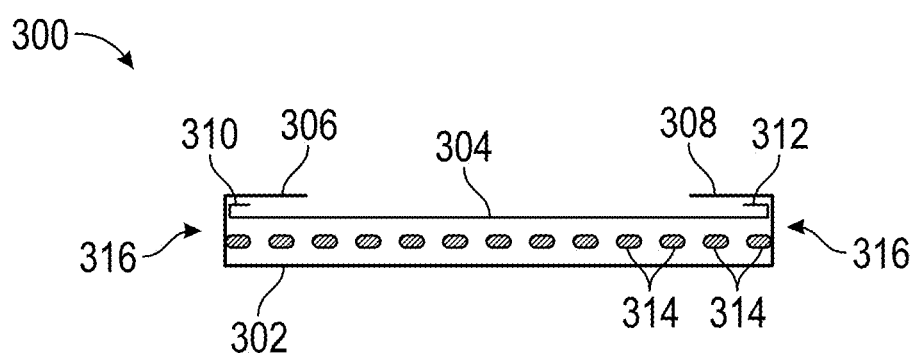
FIG. 3 depicts a schematic side view in cross-section of a patch in accordance with an embodiment of the disclosure.

FIG. 3 depicts a schematic view in cross-section of a patch 300. The patch 300 includes a first piece of nonwoven fabric 302 and a second piece of nonwoven fabric 304. The first piece of nonwoven fabric 302 includes a first longitudinal edge 306 and a second longitudinal edge 308. The second piece of nonwoven fabric 304 includes a first longitudinal edge 310 and a second longitudinal edge 312. Elastic strands 314 are disposed between the first piece of nonwoven fabric 302 and the second piece of nonwoven fabric 204. The first longitudinal edges 306, 310 are folded together at a first folded longitudinal edge 316, while the second longitudinal edges 308, 312 are folded together at a second folded longitudinal edge 318, thereby enclosing the elastic strands 314. Although the folded first longitudinal edges and folded second longitudinal edges are depicted as being folded towards one another, i.e., folded onto the second piece of nonwoven fabric 304, one or both of the folded longitudinal edges may be folded in the opposite direction, i.e., folded onto the first piece of nonwoven fabric 302.

Figure 4:
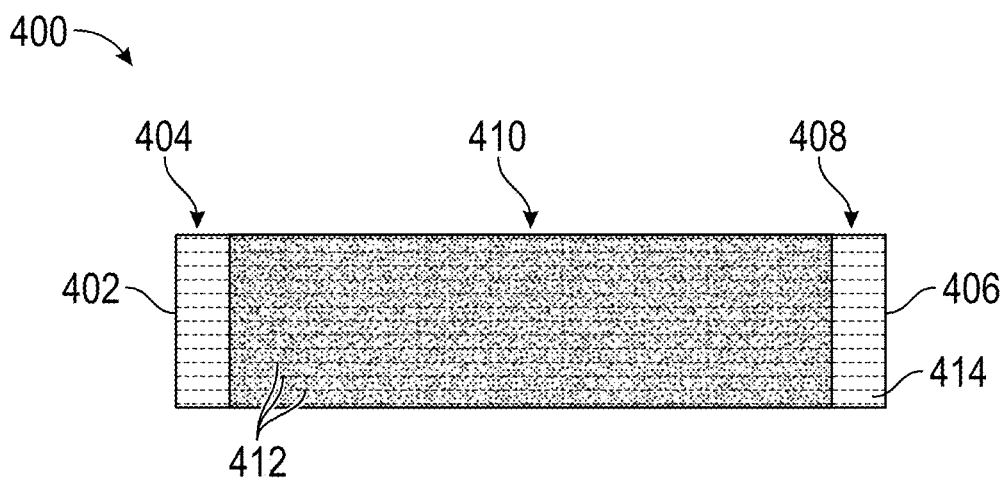
FIG. 4 depicts a schematic top view of a patch in accordance with an embodiment of the disclosure.

FIG. 4 depicts a patch 400 formed using an intermittent bonding method. Patch 400 includes a first lateral edge 402 having a first non-bonding region 404, a second lateral edge 406 having a second non-bonding region 408, and a bonding region 410 disposed in between the first and second non-bonding regions 404, 408. Each region is characterized by a plurality of elastic strands 412 either being bonded to the nonwoven material 414, i.e., in the bonding region 410, or not being bonded to the nonwoven material 414, i.e., in the non-bonding regions 404, 408. As described herein, the patch 400 may be formed using a continuous process that involves the formation of a continuous sheet of patch material that is cut at regular intervals. Thus, each non-bonding region 404, 408 in the patch 400 may be part of the same non-bonding region on the continuous sheet of patch material, but the cutting process separates the first non-bonding region of a first patch from the second non-bonding region of a second patch.

Figure 5:
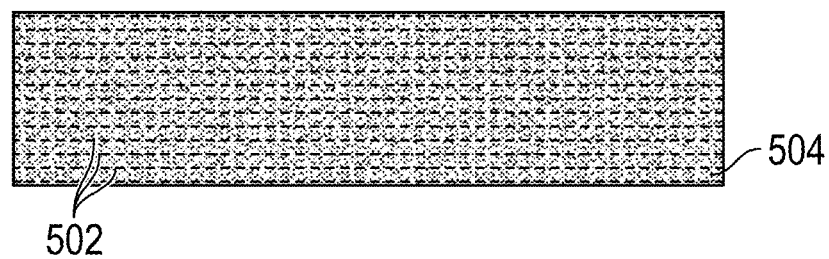
FIG. 5 depicts a schematic top view of a patch in accordance with an embodiment of the disclosure.

FIG. 5 depicts a patch 500 formed using a continuous bonding method. Patch 500 includes a plurality of elastic strands 502 bonded to a nonwoven material 504. There may be one piece of nonwoven material, two pieces of nonwoven material, or more pieces of nonwoven material depending on the needs of the application.

Figure 6:
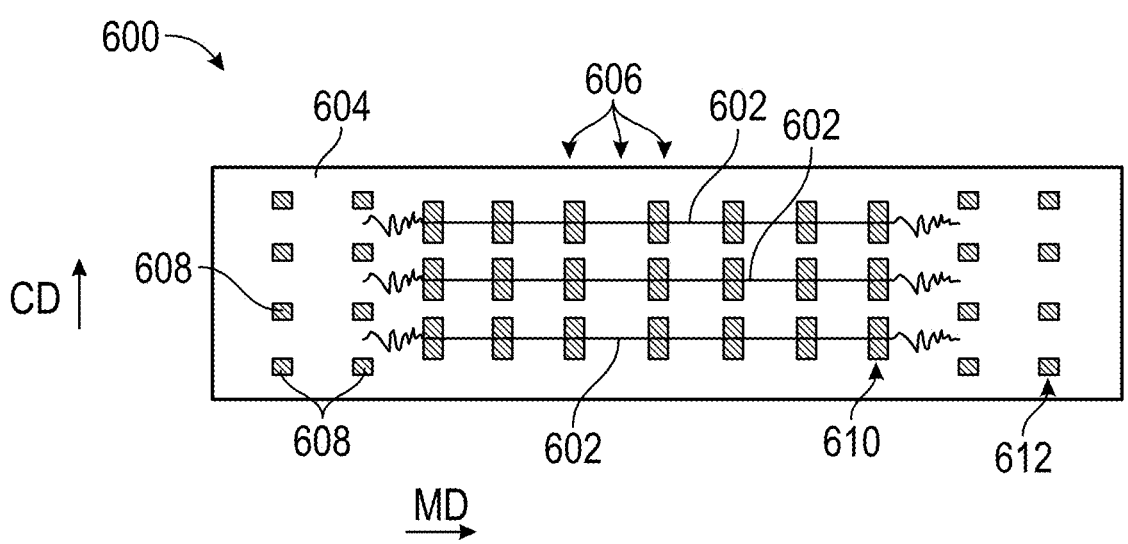
FIG. 6 depicts a schematic top view of a patch in accordance with an embodiment of the disclosure.

FIG. 6 depicts a patch 600 formed from a plurality of elastic strands 602 bonded to a nonwoven material 604 using a plurality of rows 606 of bonds 608. Since the patch 600 is formed in the machine direction, each "row" of bonds is understood with respect to this frame of reference and generally follow the cross-direction. Bonds 608 may be formed by, for example, ultrasonic bonding, thermomechanical bonding, or by the application of glue. As depicted in FIG. 6, some bonds are part of bonding pairs 610 separated by a distance configured to entrap the elastic strand and prevent lateral or longitudinal movement. Other bonds are part of non-bonding pairs 612 that are separated by a distance configured to permit an elastic strand that may be positioned therebetween to move freely in the longitudinal direction. The position of these bonds may be dictated by the features of the bonding apparatus, such as the number and position of protrusions on an anvil wheel.

Figure 7:
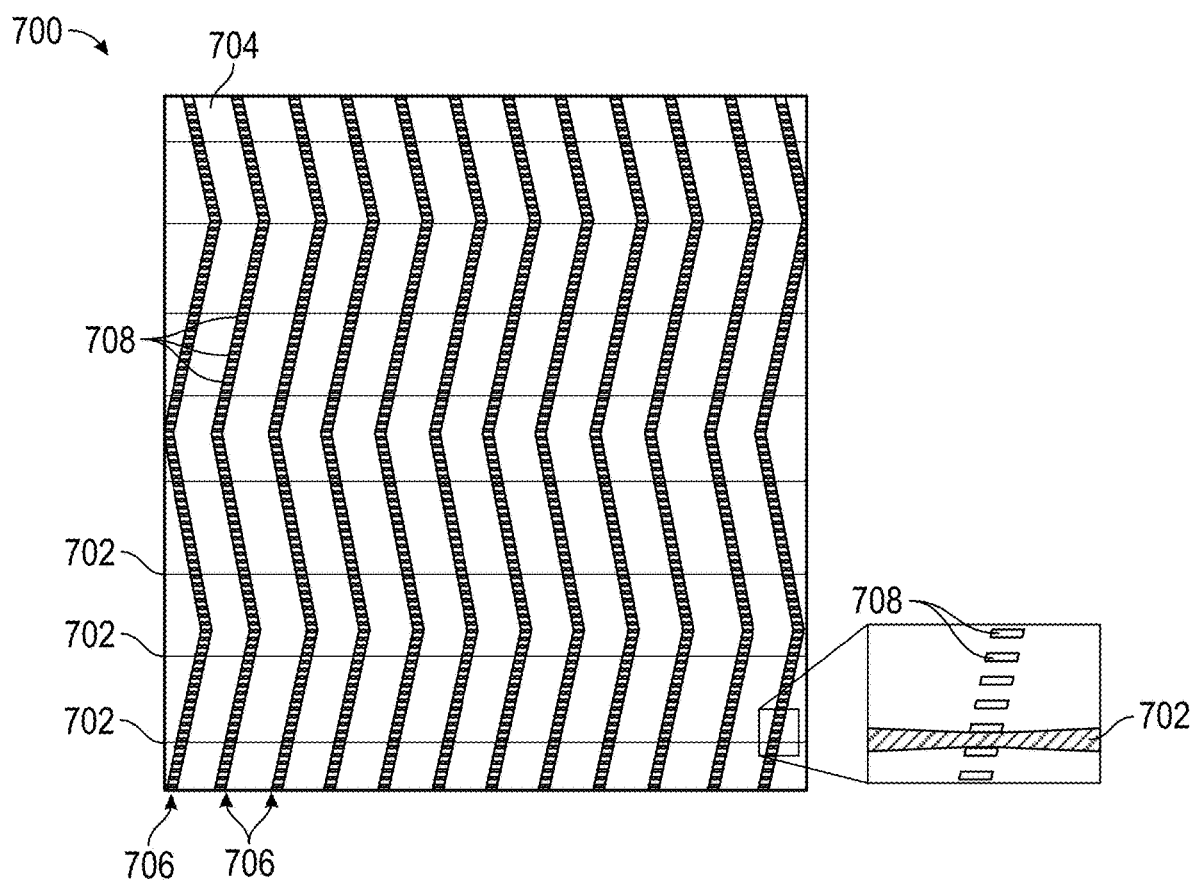
FIG. 7 depicts a top view of a patch in accordance with an embodiment of the disclosure.

FIG. 7 depicts a patch 700 formed from a plurality of elastic strands 702 bonded to a nonwoven material 704 using a plurality of rows 706 of bonds 708. As depicted in FIG. 7, the rows 706 of bonds 708 have a "zig-zag" pattern. This pattern may be favorable for, for example, ultrasonic bonding and may be formed by a rotating anvil having a plurality of protrusions such that every circumferential position on the rotating anvil includes at least one protrusion configured to form a bond. By ensuring that every circumferential position on the anvil has at least one protrusion, the ultrasonic horn may have at least one point of contact with the rotating anvil at all times, reducing the complexity of the apparatus overall.

Figure 8A:
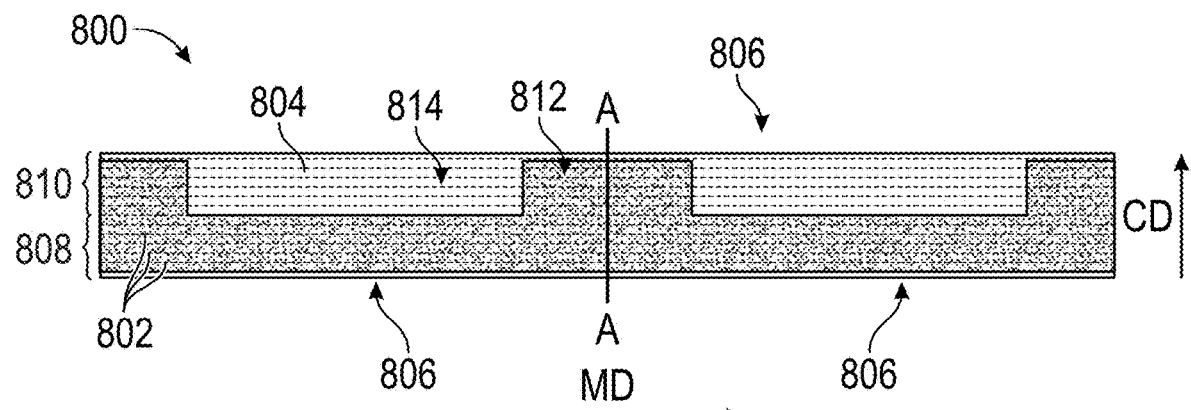
FIGS. 8A-8B depict a glue pattern applied to a patch in accordance with an embodiment of the invention.
Figure 8B:
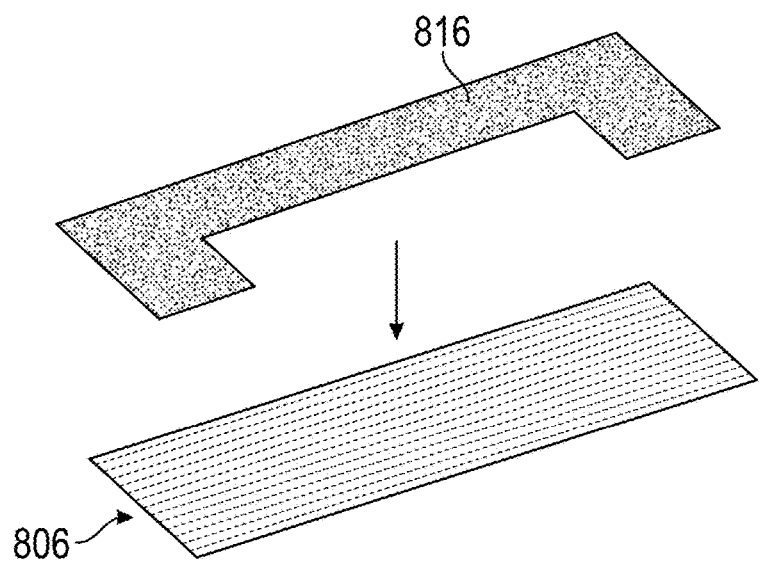

FIG. 8a depicts a continuous sheet of patch material 800 formed from a plurality of elastic strands 802 bonded to a nonwoven material 804. The continuous sheet of patch material 800 depicted in FIG. 8a includes two "patches" 806 that have not yet been cut into separate patches two patches 800. The line A-A represents the location where, in this embodiment, a cutting tool is intended to cut in order to separate patches 806. FIG. 8 further depicts the glue pattern, represented by the shaded region. As the continuous sheet of patch material 800 moves in the machine direction, glue is applied continuously across a first portion 808 and intermittently across a second portion 810, resulting in the formation of an adhering region 812 and a non-adhering region 814. After cutting the continuous sheet of patch material, the resulting glue pattern may have a "C"-shaped pattern, as illustrated in FIG. 8b, which shows the "C"-shaped glue pattern 816 positioned above the patch 806. Although the glue pattern has been described as having a "C"-shape, any other suitable shape that will result in a pocket when the patch is adhered to the absorbent article is contemplated, such as a "U"-shape, "V"-shape, or another shape having a non-adhering portion partially bound by an adhering portion.

FIGS. 9-20 depict various embodiments of an apparatus for forming an absorbent article having a pocket, as described herein. The various apparatuses enable the practicing of the various methods for forming an absorbent article having a pocket, as described herein. The embodiments in FIGS. 9-20 will now be described in more detail, with like reference numbers referring to like structures throughout.

Figure 9:
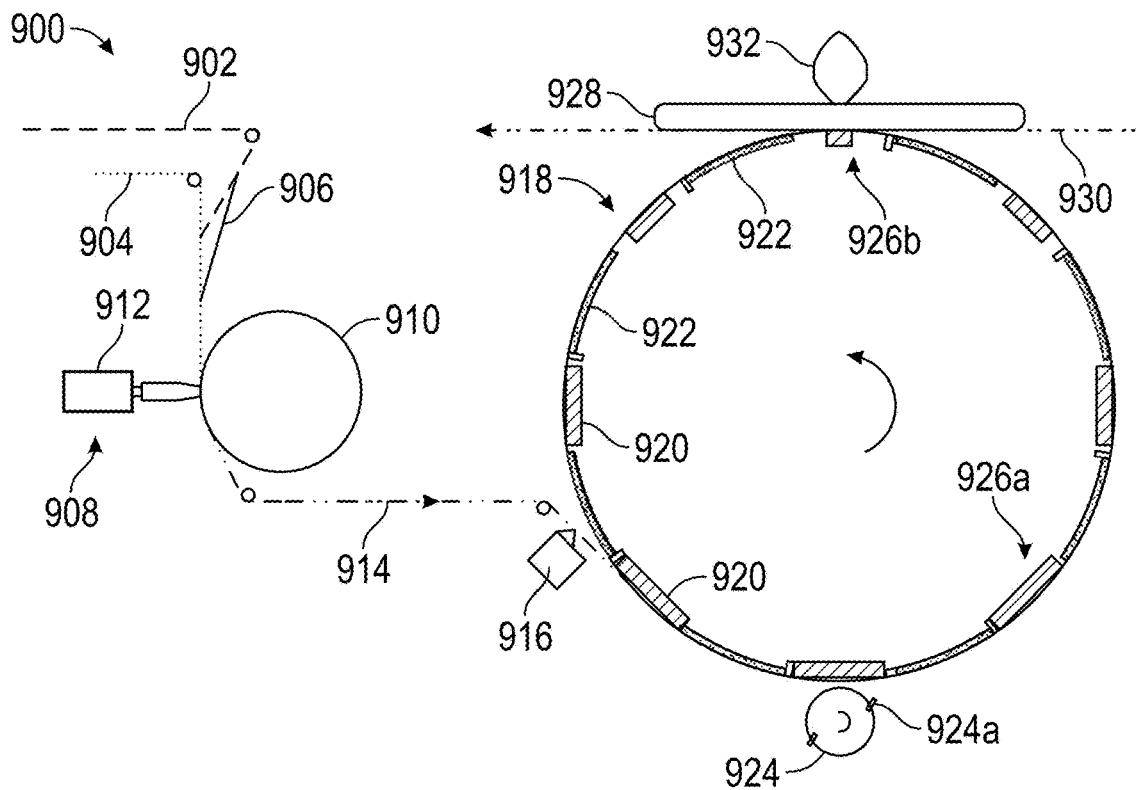
FIGS. 9-20 depict an apparatus in schematic view for producing absorbent articles having pockets in accordance with embodiments of the invention.

FIG. 9 depicts an apparatus 900 for forming a patch from a single continuous sheet of nonwoven material that is folded around a plurality of elastic strands to form a seam before the elastic strands and seam are ultrasonically bonded. The continuous sheet of patch material is passed to the cut-and-turn wheel at a lower speed than the rotation of the cut-and-turn wheel and the conveyance of the absorbent article.

Apparatus 900 includes a continuous sheet of nonwoven material 902 that is aligned with a plurality of elastic strands 904 before passing through a folding chute 906. The folded continuous sheet of nonwoven material then passes to an ultrasonic bonding apparatus 908 that includes an anvil wheel 910 and an ultrasonic horn 912. Ultrasonic bonds are formed in the ultrasonic bonding apparatus to form a continuous sheet of patch material 914. The continuous sheet of patch material 914 passes over a primary glue applicator 916 where glue is applied to the continuous sheet of patch material such that the resulting patches have a glue pattern with a non-adhering portion partially bound by an adhering portion, as depicted in FIGS. 8a-8b, for example. After glue application, the continuous sheet of patch material 914 passes to a cut-and-turn wheel 918. Cut-and-turn wheel 918 includes a plurality of rotatable vacuum pucks 920 and a plurality of static vacuum shells 922. Rotatable vacuum pucks 920 and static vacuum shells 922 pick up the continuous sheet of patch material 914 using vacuums. The cut-and-turn wheel 918 rotates in the machine direction and brings the continuous sheet of patch material 914 in contact with a cutting wheel 924, where the continuous sheet of patch material 914 is cut into discrete patches. The cutting wheel may have a number of blades 924a and may be configured to rotate at a speed coincident with the rotating speed of the cut-and-turn wheel 918 so that the continuous sheet of patch material 914 is cut at the desired positions. Each patch remains secured to one of the rotatable vacuum pucks 920 and to one of the static vacuum shells 922 while the cut-and-turn wheel 918 rotates. The rotatable vacuum puck 920 then rotates 90° from a first position 926a, where the patch is oriented with the elastic threads in the machine direction, to a second position 926b, where the patch is oriented with the elastic threads in the cross-direction. As the patch is rotated by the rotatable vacuum puck 920, the patch is permitted to slip off of the static vacuum shell 922. The cut-and-turn wheel 918 next brings the rotated patch into contact with an absorbent article 928 that has been supplied by, for example, a conveyor 930. When the patch has been aligned at the second position 926b, a phased roll 932 having an oval or oblong shape rotates and periodically presses against the absorbent article 928 to effect adhesion of the patch against the absorbent article 928. The oval or oblong shape of the phased roll enables the roll to continuously rotate and only apply force when an absorbent article and a patch are in position and capable of being adhered to one another. Upon adhesion, the absorbent article having a pocket has been formed.

Figure 10:
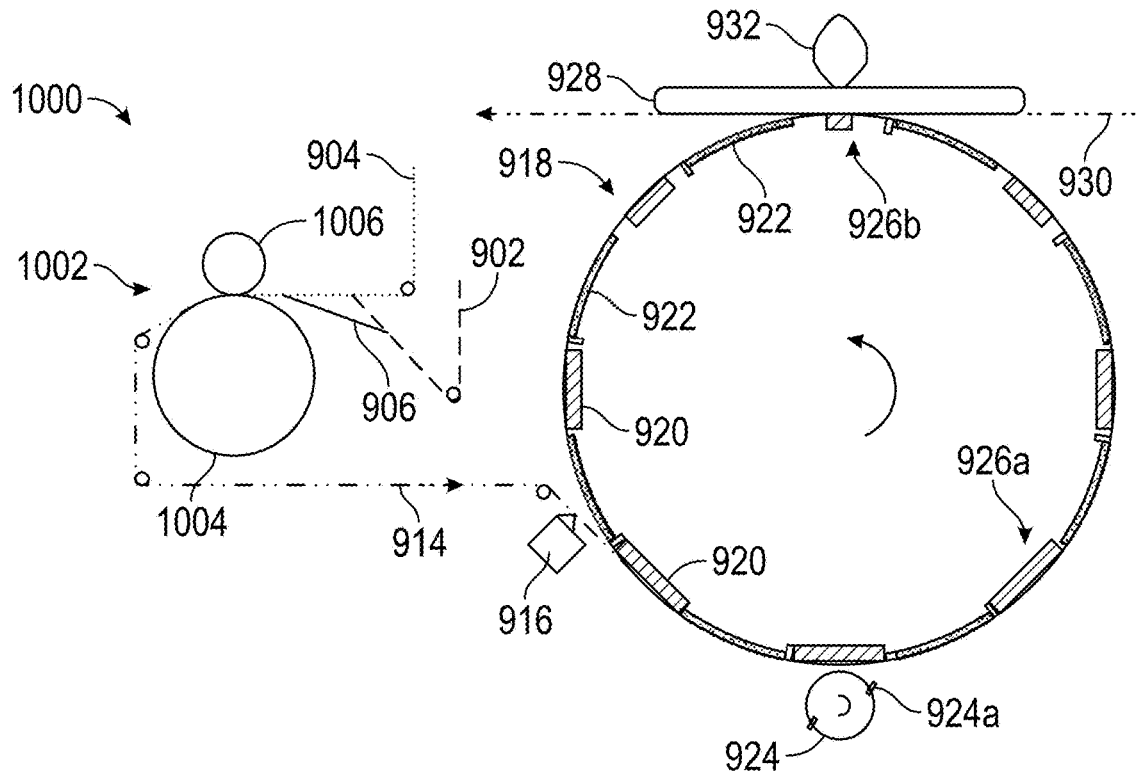

FIG. 10 depicts an apparatus 1000 for forming a patch from a single continuous sheet of nonwoven material that is folded around a plurality of elastic strands to form a seam before the elastic strands and seam are thermomechanically bonded. The continuous sheet of patch material is passed to the cut-and-turn wheel at a lower speed than the rotation of the cut-and-turn wheel and the conveyance of the absorbent article. Like numbers in FIG. 10 refer to the same or similar structures as those in FIG. 9.

Apparatus 1000 includes a continuous sheet of nonwoven material 902 that is aligned with a plurality of elastic strands 904 before passing through a folding chute 906. The folded continuous sheet of nonwoven material then passes to a thermomechanical bonding apparatus 1002 that includes an anvil wheel 1004 and heated wheel 1006 configured to press against the folded continuous sheet of nonwoven material to bond the materials together, as described herein. Thermomechanical bonds are formed in the thermomechanical bonding apparatus to form a continuous sheet of patch material 914. This continuous sheet of patch material 914 proceeds to primary glue applicator 916 and cut-and-turn wheel 918, as described with respect to FIG. 9.

Figure 11:
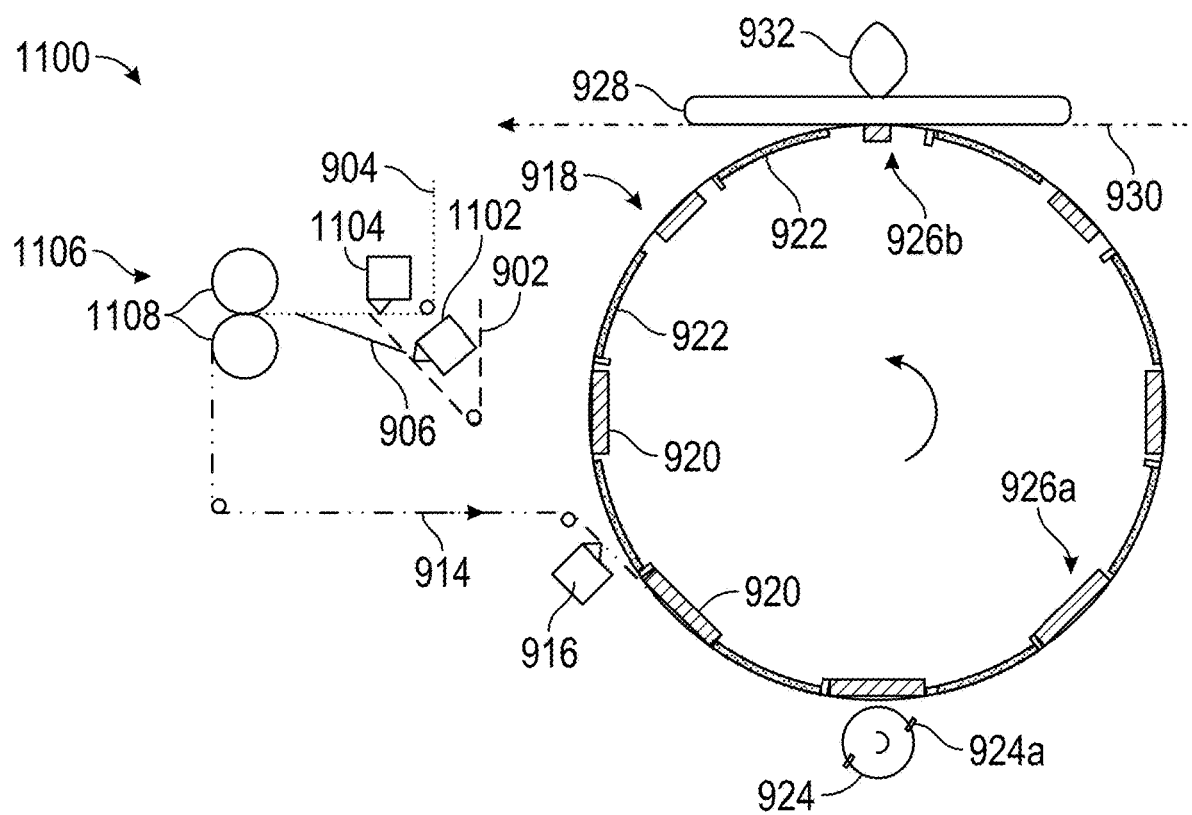

FIG. 11 depicts an apparatus 1100 for forming a patch from a single continuous sheet of nonwoven material that is folded around a plurality of elastic strands to form a seam before the elastic strands and seam are glued. The continuous sheet of patch material is passed to the cut-and-turn wheel at a lower speed than the rotation of the cut-and-turn wheel and the conveyance of the absorbent article. Like numbers in FIG. 11 refer to the same or similar structures as those in FIGS. 9 and 10.

Apparatus 1100 includes a continuous sheet of nonwoven material 902 that passes through a first glue applicator 1102 and a plurality of elastic strands 904 that passes through a second glue applicator 1104. The continuous sheet of nonwoven material 902 is then aligned with the plurality of elastic strands 904 before passing through a folding chute 906. The folded continuous sheet of nonwoven material then passes to a pressing apparatus 1106 that includes a pair of pressing wheel 1108 configured to press against the folded continuous sheet of nonwoven material to effectuate adhesion of the materials via the glue that was applied by glue applicators 1102, 1104, thereby forming a continuous sheet of patch material 914. This continuous sheet of patch material 914 proceeds to primary glue applicator 916 and cut-and-turn wheel 918, as described with respect to FIGS. 9 and 10.

Figure 12:
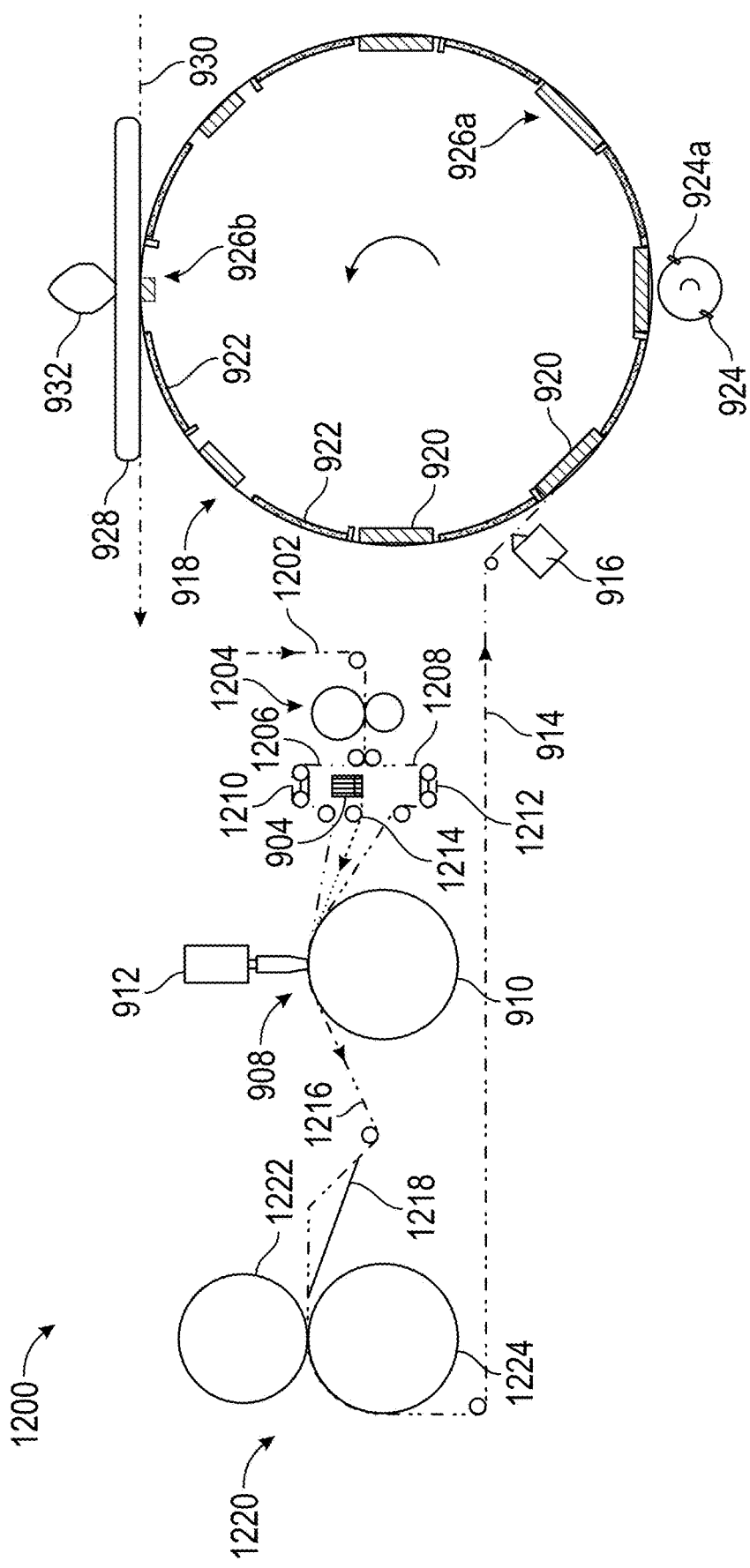

FIG. 12 depicts an apparatus 1200 for forming a patch from a single continuous source of nonwoven material that is slit into two continuous sheets of nonwoven material that is aligned around a plurality of elastic strands before the elastic strands are ultrasonically bonded. The continuous sheet of bonded elastic nonwoven material is passed through a folding chute to fold the first and second longitudinal edges before the longitudinal edges are thermomechanically bonded. The continuous sheet of patch material is passed to the cut-and-turn wheel at a lower speed than the rotation of the cut-and-turn wheel and the conveyance of the absorbent article. Like numbers in FIG. 12 refer to the same or similar structures as those in FIGS. 9-11.

Apparatus 1200 includes a continuous source of nonwoven material 1202 that passes through a slitter 1204 that slits the continuous source of nonwoven material 1202 into a first continuous sheet of nonwoven material 1206 and a second continuous sheet of nonwoven material 1208. First continuous sheet of nonwoven material 1206 is aligned by a first steering guide 1210, second continuous sheet of nonwoven material 1208 is aligned by a second steering guide 1212, and a plurality of elastic strands 904 is aligned by a third steering guide 1214. After alignment, the first and second continuous sheets of nonwoven material 1206, 1208 and plurality of elastic strands 904 pass to an ultrasonic bonding apparatus 908 that includes an anvil wheel 910 and an ultrasonic horn 912. Ultrasonic bonds are formed in the ultrasonic bonding apparatus to form a continuous sheet of bonded elastic nonwoven material 1216, which next pass through a folding chute 1218 configured to fold a first longitudinal edge of the continuous sheet of bonded elastic nonwoven material 1216 and a second longitudinal of the continuous sheet of bonded elastic nonwoven material 1216, as described herein. The folded continuous sheet of bonded elastic nonwoven material passes to a thermomechanical bonding apparatus 1220 that includes an anvil wheel 1222 and a heated wheel 1224 configured to press against the folded continuous sheet of bonded elastic nonwoven material and bond the first and second folded longitudinal edges, thereby forming the continuous sheet of patch material 914. This continuous sheet of patch material 914 proceeds to primary glue applicator 916 and cut-and-turn wheel 918, as described with respect to FIGS. 9-11.

Figure 13:
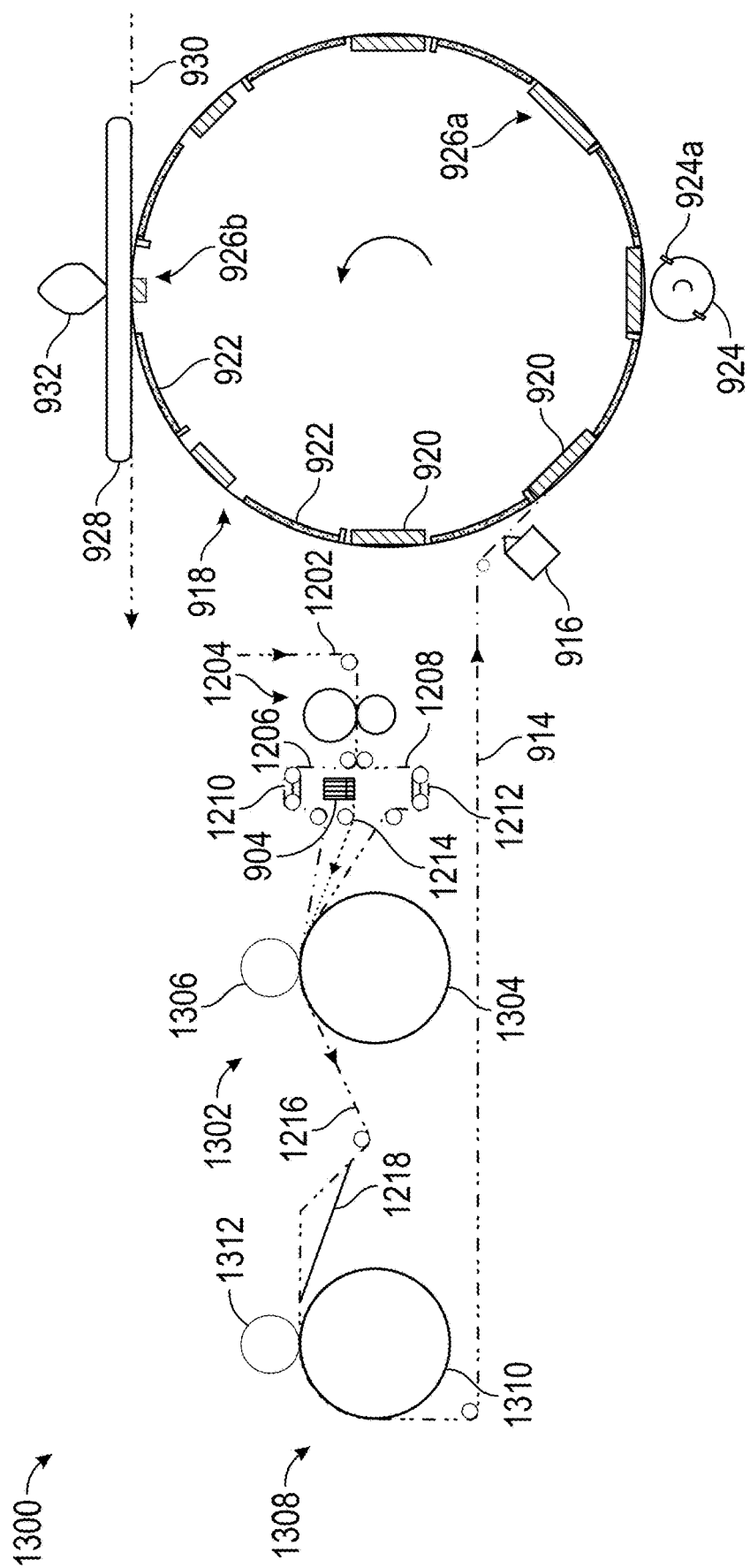

FIG. 13 depicts an apparatus 1300 for forming a patch from a single continuous source of nonwoven material that is slit into two continuous sheets of nonwoven material that is aligned around a plurality of elastic strands before the elastic strands are thermomechanically bonded. The continuous sheet of bonded elastic nonwoven material is passed through a folding chute to fold the first and second longitudinal edges before the longitudinal edges are thermomechanically bonded. The continuous sheet of patch material is passed to the cut-and-turn wheel at a lower speed than the rotation of the cut-and-turn wheel and the conveyance of the absorbent article. Like numbers in FIG. 13 refer to the same or similar structures as those in FIGS. 9-12.

Apparatus 1300 includes a continuous source of nonwoven material 1202 that passes through a slitter 1204 that slits the continuous source of nonwoven material 1202 into a first continuous sheet of nonwoven material 1206 and a second continuous sheet of nonwoven material 1208. First continuous sheet of nonwoven material 1206 is aligned by a first steering guide 1210, second continuous sheet of nonwoven material 1208 is aligned by a second steering guide 1212, and a plurality of elastic strands 904 is aligned by a third steering guide 1214. After alignment, the first and second continuous sheets of nonwoven material 1206, 1208 and plurality of elastic strands 904 pass to a first thermomechanical bonding apparatus 1302 that includes an anvil wheel 1304 and a heated wheel 1306. Thermomechanical bonds are formed in the thermomechanical bonding apparatus to form a continuous sheet of bonded elastic nonwoven material 1216, which next pass through a folding chute 1218 configured to fold a first longitudinal edge of the continuous sheet of bonded elastic nonwoven material 1216 and a second longitudinal of the continuous sheet of bonded elastic nonwoven material 1216, as described herein. The folded continuous sheet of bonded elastic nonwoven material passes to a second thermomechanical bonding apparatus 1308 that includes an anvil wheel 1310 and a heated wheel 1312 configured to press against the folded continuous sheet of bonded elastic nonwoven material and bond the first and second folded longitudinal edges, thereby forming the continuous sheet of patch material 914. This continuous sheet of patch material 914 proceeds to primary glue applicator 916 and cut-and-turn wheel 918, as described with respect to FIGS. 9-12.

Figure 14:
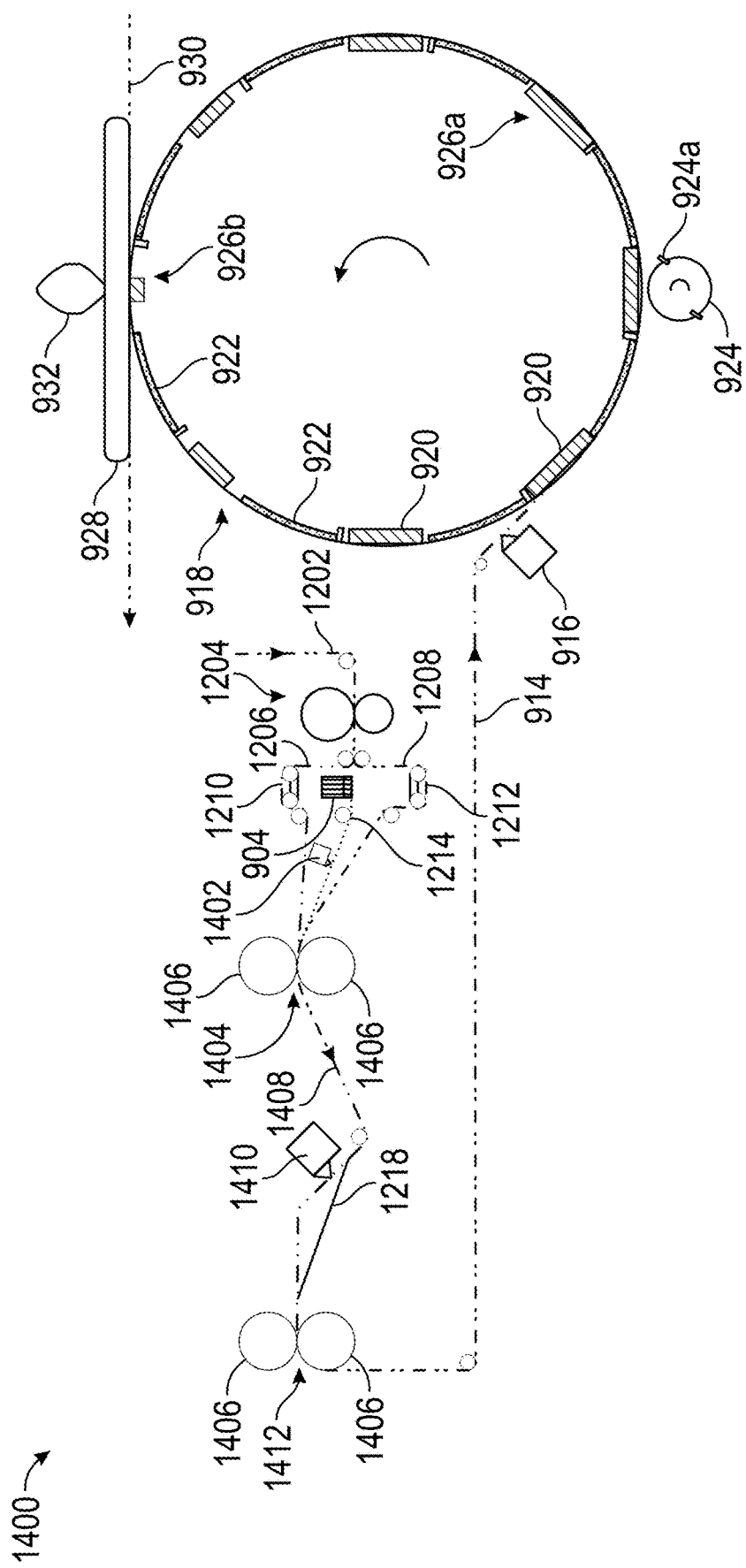

FIG. 14 depicts an apparatus 1400 for forming a patch from a single continuous source of nonwoven material which is slit into two continuous sheets of nonwoven material that is aligned around a plurality of elastic strands before the elastic strands are glued. The continuous sheet of bonded elastic nonwoven material is passed through a folding chute to fold the first and second longitudinal edges before the longitudinal edges are glued. The continuous sheet of patch material is passed to the cut-and-turn wheel at a lower speed than the rotation of the cut-and-turn wheel and the conveyance of the absorbent article. Like numbers in FIG. 14 refer to the same or similar structures as those in FIGS. 9-13.

Apparatus 1400 includes a continuous source of nonwoven material 1202 that passes through a slitter 1204 that slits the continuous source of nonwoven material 1202 into a first continuous sheet of nonwoven material 1206 and a second continuous sheet of nonwoven material 1208. First continuous sheet of nonwoven material 1206 is aligned by a first steering guide 1210 and second continuous sheet of nonwoven material 1208 is aligned by a second steering guide 1212. A first glue applicator 1402 applies glue to a plurality of elastic strands 904, which are then aligned by a third steering guide 1214. After alignment, the first and second continuous sheets of nonwoven material 1206, 1208 and plurality of elastic strands 904 pass to a first pair 1404 of pressing rolls 1406 that press the first and second continuous sheets of nonwoven material 1206, 1208 and plurality of elastic strands 904 together to form a continuous sheet of glued elastic nonwoven material 1408. A second glue applicator 1410 applies glue to the continuous sheet of glued elastic nonwoven material 1408, which next passes through a folding chute 1218 configured to fold a first longitudinal edge of the continuous sheet of glued elastic nonwoven material 1408 and a second longitudinal of the continuous sheet of glued elastic nonwoven material 1408, as described herein. The folded continuous sheet of glued elastic nonwoven material passes to a second pair 1412 of pressing rolls 1406 configured to press against the folded continuous sheet of glued elastic nonwoven material and effect adhesion of the first and second folded longitudinal edges, thereby forming the continuous sheet of patch material 914. This continuous sheet of patch material 914 proceeds to primary glue applicator 916 and cut-and-turn wheel 918, as described with respect to FIGS. 9-13.

Figure 15:
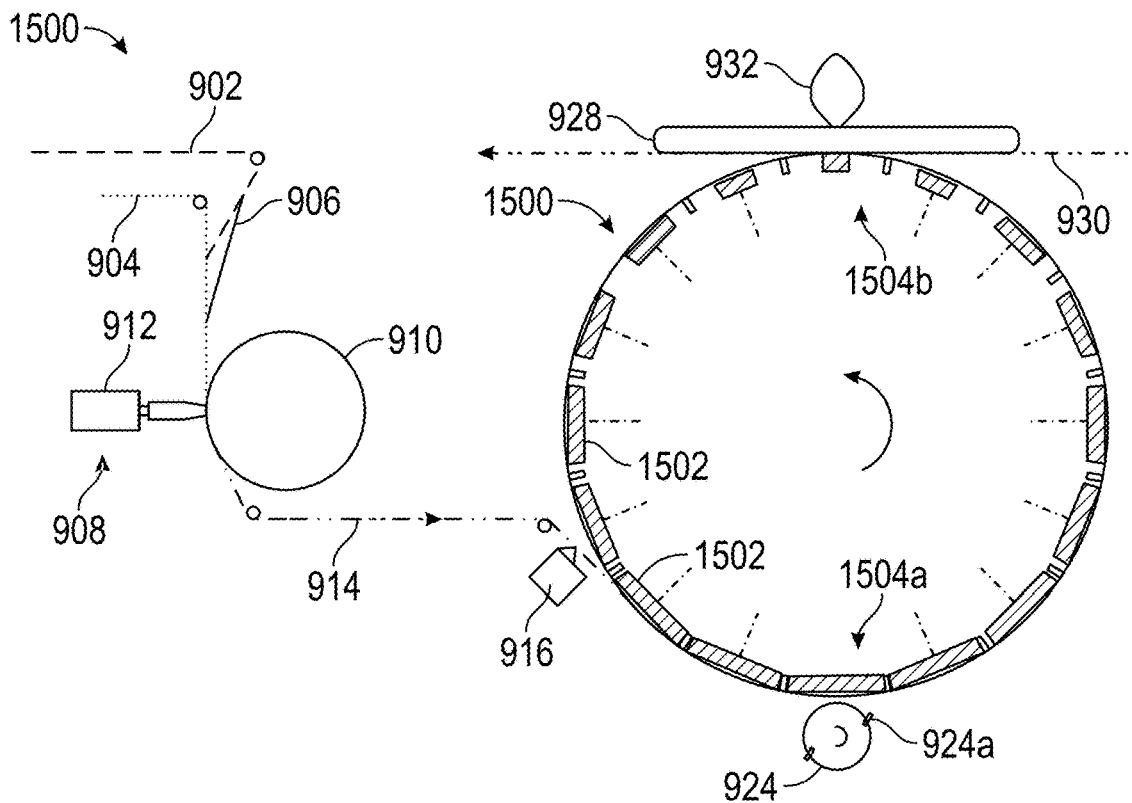

FIG. 15 depicts an apparatus 1500 for forming a patch from a single continuous sheet of nonwoven material that is folded around a plurality of elastic strands to form a seam before the elastic strands and seam are ultrasonically bonded. The continuous sheet of patch material is passed to the cut-and-turn wheel at the same speed as the rotation of the cut-and-turn wheel, but at a lower speed than the conveyance of the absorbent article. Like numbers in FIG. 15 refer to the same or similar structures as those in FIGS. 9-14.

Apparatus 1500 includes patch-forming structures for the production of a continuous sheet of patch material 914, as described with respect to FIG. 9. After glue application, the continuous sheet of patch material 914 passes to a cut-and-turn wheel 1500. Cut-and-turn wheel 1500 includes a plurality of rotatable vacuum pucks 1502. Since cut-and-turn wheel 1500 moves at the same speed as the continuous sheet of patch material 914, the static vacuum shells in FIG. 9 are not necessary. Rotatable vacuum pucks 1502 pick up the continuous sheet of patch material 914 using vacuums. The cut-and-turn wheel 1500 rotates in the machine direction and brings the continuous sheet of patch material 914 in contact with a cutting wheel 924, where the continuous sheet of patch material 914 is cut into discrete patches. The cutting wheel may have a number of blades 924a and may be configured to rotate at a speed coincident with the rotating speed of the cut-and-turn wheel 918 so that the continuous sheet of patch material 914 is cut at the desired positions. Each patch remains secured to one of the rotatable vacuum pucks 1502 while the cut-and-turn wheel 1500 rotates. The rotatable vacuum puck 1502 then rotates 90° from a first position 1504a, where the patch is oriented with the elastic threads in the machine direction, to a second position 1504b, where the patch is oriented with the elastic threads in the cross-direction. The cut-and-turn wheel 1500 next brings the rotated patch into contact with an absorbent article 928 that has been supplied by, for example, a conveyor 930. When the patch has been aligned at the second position 1504b, a phased roll 932 having an oval or oblong shape rotates and periodically presses against the absorbent article 928 to effect adhesion of the patch against the absorbent article 928. The oval or oblong shape of the phased roll enables the roll to continuously rotate and only apply force when an absorbent article and a patch are in position and capable of being adhered to one another. Upon adhesion, the absorbent article having a pocket has been formed.

Figure 16:
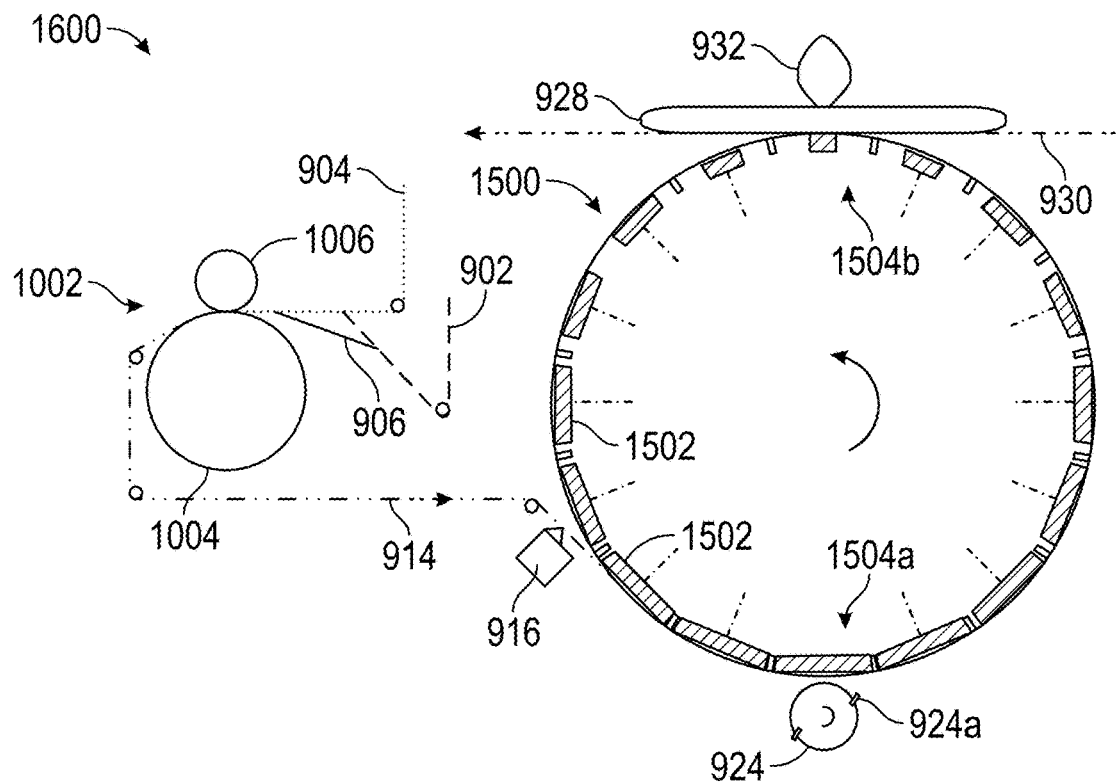

FIG. 16 depicts an apparatus 1600 for forming a patch from a single continuous sheet of nonwoven material that is folded around a plurality of elastic strands to form a seam before the elastic strands and seam are thermomechanically bonded. The continuous sheet of patch material is passed to the cut-and-turn wheel at the same speed as the rotation of the cut-and-turn wheel, but at a lower speed than the conveyance of the absorbent article. Like numbers in FIG. 16 refer to the same or similar structures as those in FIGS. 9-15.

Apparatus 1600 includes patch-forming structures for the production of a continuous sheet of patch material 914, as described with respect to FIG. 10. This continuous sheet of patch material 914 is glued, cut, and patches affixed to an absorbent article, as described with respect to FIG. 15.

Figure 17:
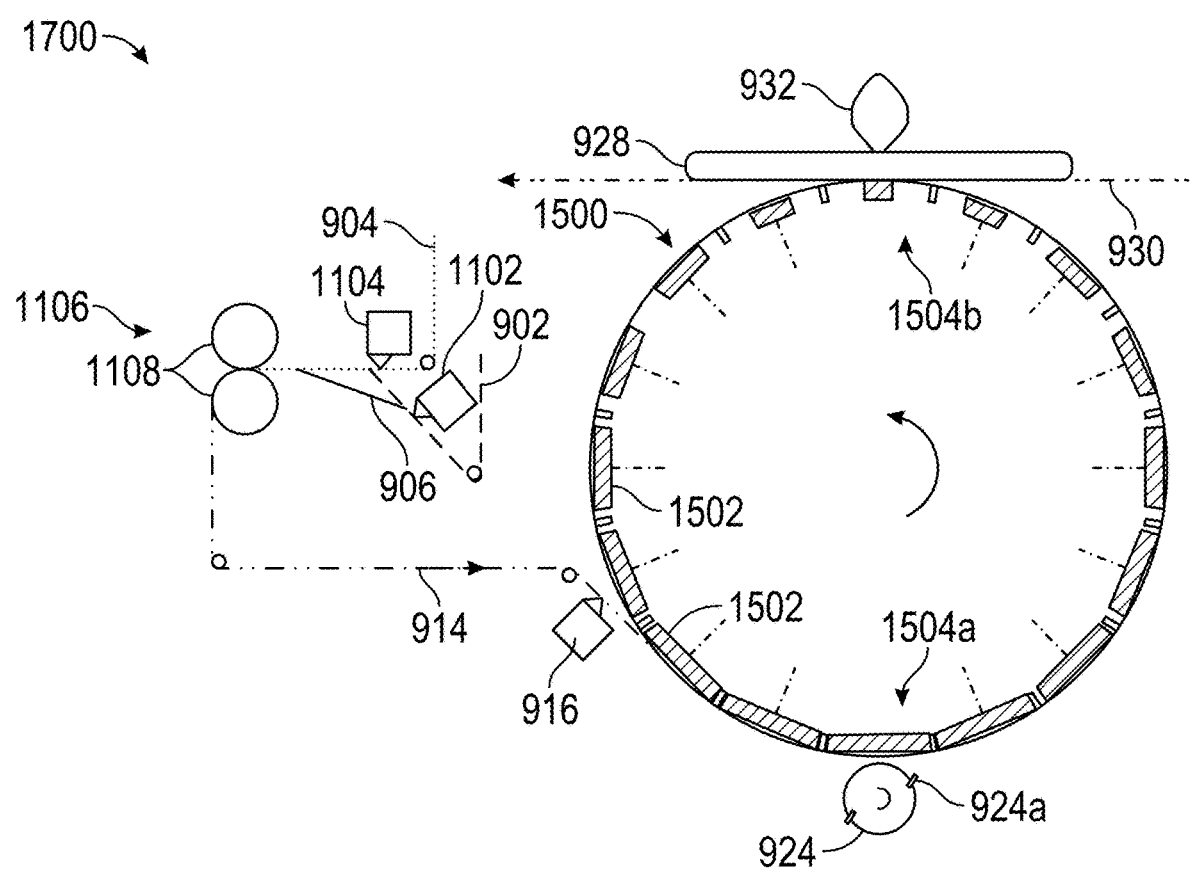

FIG. 17 depicts an apparatus 1700 for forming a patch from a single continuous sheet of nonwoven material that is folded around a plurality of elastic strands to form a seam before the elastic strands and seam are glued. The continuous sheet of patch material is passed to the cut-and-turn wheel at the same speed as the rotation of the cut-and-turn wheel, but at a lower speed than the conveyance of the absorbent article. Like numbers in FIG. 17 refer to the same or similar structures as those in FIGS. 9-16.

Apparatus 1700 includes patch-forming structures for the production of a continuous sheet of patch material 914, as described with respect to FIG. 11. This continuous sheet of patch material 914 is glued, cut, and patches affixed to an absorbent article, as described with respect to FIG. 15.

Figure 18:
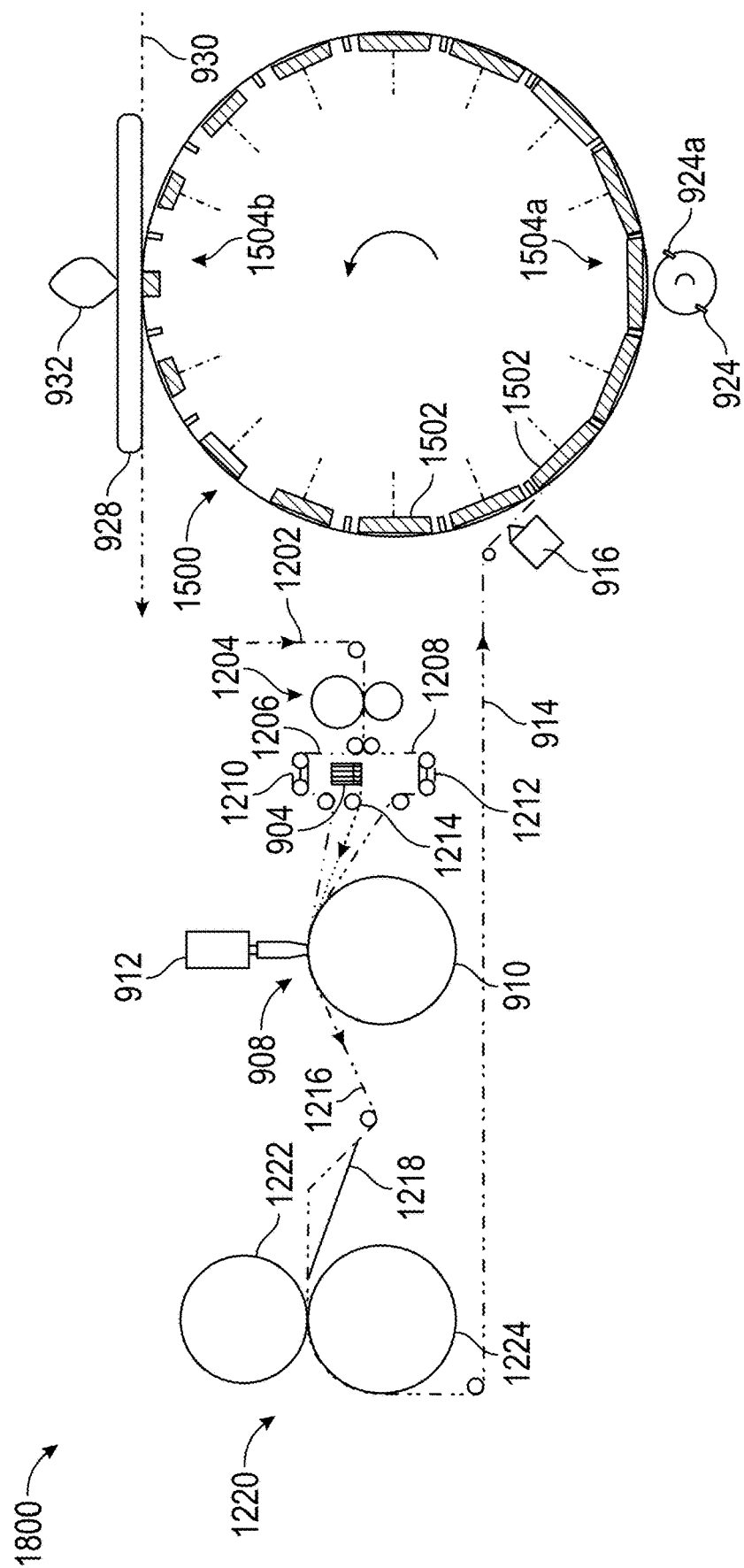

FIG. 18 depicts an apparatus 1800 for forming a patch from a single continuous source of nonwoven material which is slit into two continuous sheets of nonwoven material that is aligned around a plurality of elastic strands before the elastic strands are ultrasonically bonded. The continuous sheet of bonded elastic nonwoven material is passed through a folding chute to fold the first and second longitudinal edges before the longitudinal edges are thermomechanically bonded. The continuous sheet of patch material is passed to the cut-and-turn wheel at the same speed as the rotation of the cut-and-turn wheel, but at a lower speed than the conveyance of the absorbent article. Like numbers in FIG. 18 refer to the same or similar structures as those in FIGS. 9-17.

Apparatus 1800 includes patch-forming structures for the production of a continuous sheet of patch material 914, as described with respect to FIG. 12. This continuous sheet of patch material 914 is glued, cut, and patches affixed to an absorbent article, as described with respect to FIG. 15.

Figure 19:
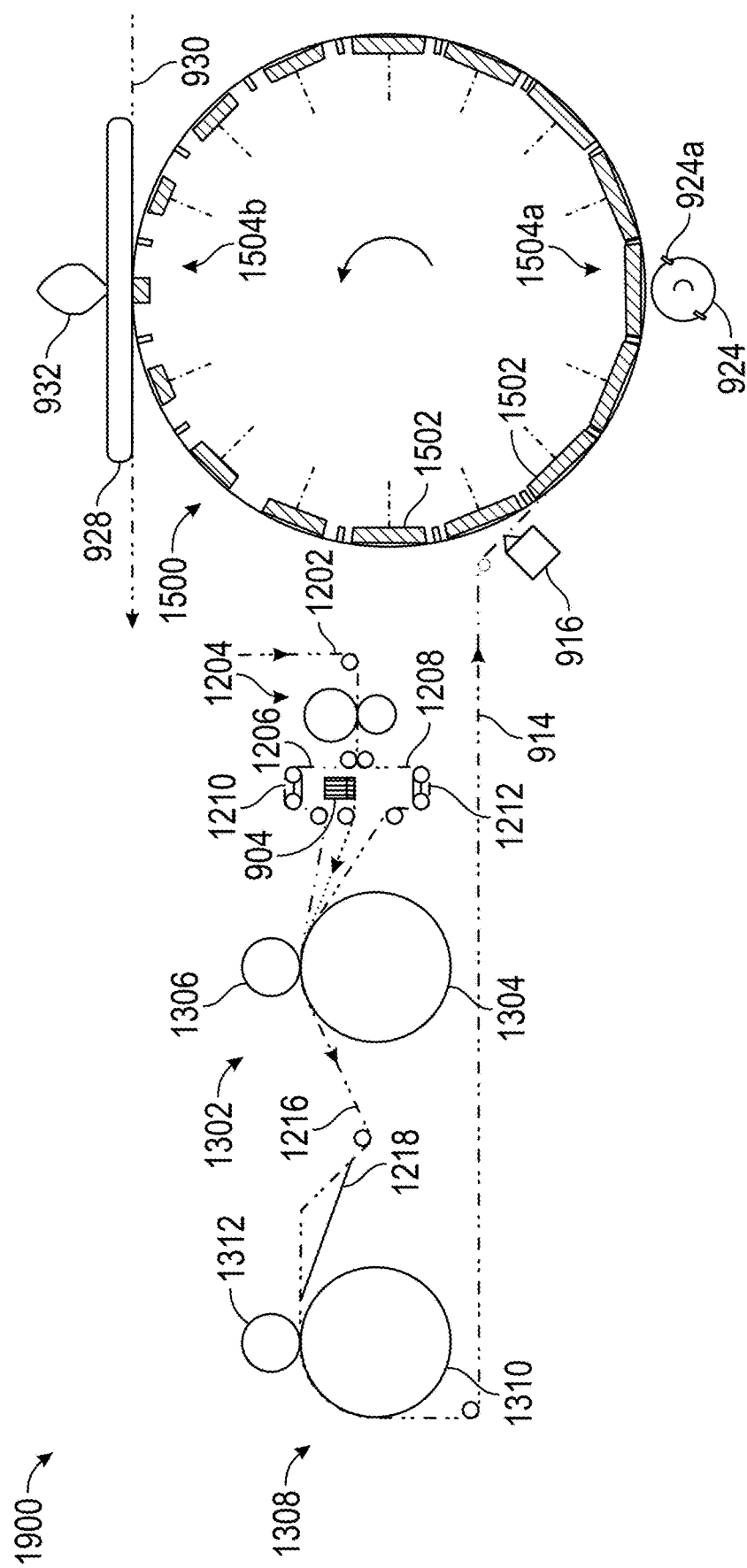

FIG. 19 depicts an apparatus 1900 for forming a patch from a single continuous source of nonwoven material which is slit into two continuous sheets of nonwoven material that is aligned around a plurality of elastic strands before the elastic strands are thermomechanically bonded. The continuous sheet of bonded elastic nonwoven material is passed through a folding chute to fold the first and second longitudinal edges before the longitudinal edges are thermomechanically bonded. The continuous sheet of patch material is passed to the cut-and-turn wheel at the same speed as the rotation of the cut-and-turn wheel, but at a lower speed than the conveyance of the absorbent article. Like numbers in FIG. 19 refer to the same or similar structures as those in FIGS. 9-18.

Apparatus 1900 includes patch-forming structures for the production of a continuous sheet of patch material 914, as described with respect to FIG. 13. This continuous sheet of patch material 914 is glued, cut, and patches affixed to an absorbent article, as described with respect to FIG. 15.

Figure 20:
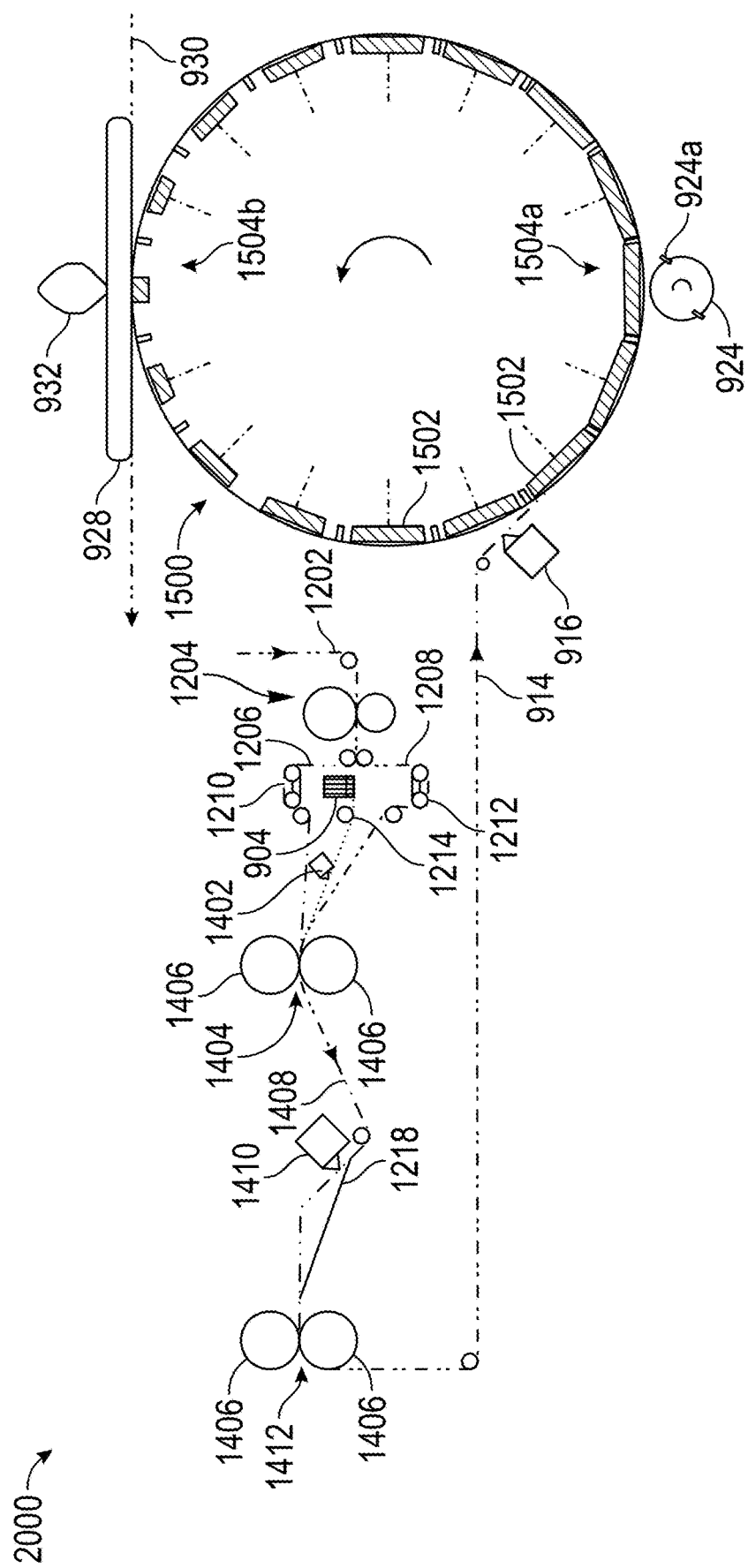

FIG. 20 depicts an apparatus 2000 for forming a patch from a single continuous source of nonwoven material which is slit into two continuous sheets of nonwoven material that is aligned around a plurality of elastic strands before the elastic strands are glued. The continuous sheet of bonded elastic nonwoven material is passed through a folding chute to fold the first and second longitudinal edges before the longitudinal edges are glued. The continuous sheet of patch material is passed to the cut-and-turn wheel at the same speed as the rotation of the cut-and-turn wheel, but at a lower speed than the conveyance of the absorbent article. Like numbers in FIG. 20 refer to the same or similar structures as those in FIGS. 9-19.

Apparatus 2000 includes patch-forming structures for the production of a continuous sheet of patch material 914, as described with respect to FIG. 14. This continuous sheet of patch material 914 is glued, cut, and patches affixed to an absorbent article, as described with respect to FIG. 15.

EMBODIMENTS

The following is a listing of non-limiting embodiments.
Methods for Producing Absorbent Articles Embodiment 1. A method for producing an absorbent article having a pocket, the method comprising, consisting essentially of, or consisting of:
    producing a patch, the patch comprising at least one nonwoven layer and a plurality of elastic strands bonded to the at least nonwoven layer, and
    adhering the patch to an absorbent article to form a pocket.

Embodiment 2. The method of embodiment 1, wherein producing the patch comprises, consists essentially of, or consists of:
    providing at least one continuous sheet of nonwoven material in a machine direction (MD);

providing a plurality of elastic strands in the MD and positioning the plurality of elastic strands on the at least one continuous sheet of nonwoven material;

bonding the plurality of elastic strands to the at least one continuous sheet of nonwoven material to form a continuous sheet of patch material; and cutting the continuous sheet of patch material at regular intervals in a cross-direction (CD) to produce a plurality of patches.

Embodiment 3. The method of embodiment 2, wherein exactly one continuous sheet of nonwoven material is provided, and wherein the method further comprises, consists essentially of, or consists of:

after positioning the plurality of elastic strands on the continuous sheet of nonwoven material, folding the continuous sheet of nonwoven material around the plurality of elastic strands, wherein the folding is in the CD such that a first longitudinal edge of the continuous sheet of nonwoven material overlaps a second longitudinal edge of the continuous sheet of nonwoven material, thereby forming a seam running in the MD, and wherein each elastic strand is positioned between an upper portion of the continuous nonwoven material and a lower portion of the continuous nonwoven material; and bonding the seam in the continuous sheet of nonwoven material and the plurality of elastic strands to the folded continuous sheet of nonwoven material such that the plurality of elastic strands is bonded between the upper portion of the continuous nonwoven material and the lower portion of the continuous nonwoven material.

Embodiment 4. The method of embodiment 3, wherein the seam is bonded using glue, thermobonding, and/or ultrasonic bonding.

Embodiment 5. The method of embodiment 2, wherein first and second continuous sheets of nonwoven material are provided, and wherein the method further comprises, consists essentially of, or consists of:

positioning the plurality of elastic strands between the first continuous sheet of nonwoven material and the second continuous sheet of nonwoven material such that the first continuous sheet of nonwoven material and second continuous sheet of nonwoven material substantially overlap one another;

bonding the plurality of elastic strands between the first continuous sheet of nonwoven material and the second continuous sheet of nonwoven material;

folding a first longitudinal edge of the first continuous sheet of nonwoven material and a first longitudinal edge of the second continuous sheet of nonwoven material, which first longitudinal edges are overlapping, and bonding the folded first longitudinal edges to the first continuous sheet of nonwoven material; and folding a second longitudinal edge of the first continuous sheet of nonwoven material and a second longitudinal edge of the second continuous sheet of nonwoven material, which second longitudinal edges are overlapping, and bonding the folded second longitudinal edges to the first continuous sheet of nonwoven material.

Embodiment 6. The method of embodiment 5, wherein the folded first longitudinal edges and the folded second longitudinal edges are bonded using glue, thermobonding, and/or ultrasonic bonding.

Embodiment 7. The method of embodiment 2, wherein the plurality of elastic strands are bonded to the at least one continuous sheet of nonwoven material using glue, thermobonding, and/or ultrasonic bonding.

Embodiment 8. The method of embodiment 7, wherein the bonding is thermobonding or ultrasonic bonding, and wherein bonding the plurality of elastic strands comprises, consists essentially of, or consists of forming a plurality of bond pairs, each bond pair comprising, consisting essentially of, or consisting of a first bond and a second bond separated by a distance configured to entrap an elastic strand therebetween in a tensioned state.

Embodiment 9. The method of embodiment 8, wherein bonding the plurality of elastic strands further comprises, consists essentially of, or consists of forming a plurality of non-bonding pairs, each non-bonding pair comprising, consisting essentially of, or consisting of a first bond and a second bond separated by a distance configured to permit an elastic strand positioned therebetween to tension and relax without restriction.

Embodiment 10. The method of embodiment 8, wherein a portion of the plurality of bond pairs do not have an elastic strand entrapped therebetween.

Embodiment 11. The method of embodiment 2, wherein the plurality of elastic strands are continuously bonded to the at least one continuous sheet of nonwoven material.

Embodiment 12. The method of embodiment 2, wherein the plurality of elastic strands are intermittently bonded to the at least one continuous sheet of nonwoven material such that, after cutting the continuous sheet of nonwoven material, the patch has a first lateral edge without bonds, a central portion with bonds, and a second lateral edge without bonds.

Embodiment 13. The method of embodiment 1, wherein adhering the patch to the absorbent article comprises, consists essentially of, or consists of:

providing a plurality of absorbent articles in a machine direction (MD);

applying glue to a continuous sheet of patch material;

supplying the continuous sheet of patch material to an alignment wheel;

cutting the continuous sheet of patch material at regular intervals in a cross-direction (CD) to produce a plurality of patches;

rotating each patch in the plurality of patches 90°;

aligning one patch in the plurality of patches with one absorbent article in the plurality of absorbent articles; and pressing the patch against the absorbent article.

Embodiment 14. The method of embodiment 13, wherein applying glue to the continuous sheet of patch material comprises, consists essentially of, or consists of moving the continuous sheet of patch material in the MD across a glue applicator, wherein the glue applicator is configured to apply glue continuously across a first portion of the continuous sheet of patch material and to apply glue intermittently across a second portion of the continuous sheet of patch material.

Embodiment 15. The method of embodiment 14, wherein cutting the continuous sheet of patch material comprises, consists essentially of, or consists of cutting each intermittently applied amount of glue in the second portion in approximately two equal sizes so that a "C"-shaped pattern of glue is present on each patch in the plurality of patches.

Embodiment 16. The method of embodiment 13, wherein aligning the patch with the absorbent article comprises, consists essentially of, or consists of supplying the continuous sheet of patch material to the alignment wheel at a first speed, moving the patch in the MD on the alignment wheel at a second speed, and moving the absorbent article in the MD at a third speed.

Embodiment 17. The method of embodiment 16, wherein the second speed is equal to the third speed such that the elastic patch is unstretched in the MD when pressed against the absorbent article.

Embodiment 18. The method of embodiment 16, wherein the first speed is equal to the second speed and the second speed is lower than the third speed such that the elastic patch is stretched when pressed against the absorbent article.

Embodiment 19. The method of embodiment 13, wherein aligning the patch with the absorbent article comprises, consists essentially of, or consists of aligning the patch with an inner surface of the absorbent article, wherein the inner surface is configured to contact a user when in use.

Embodiment 20. The method of embodiment 15, wherein aligning the patch with the absorbent article comprises, consists essentially of, or consists of aligning the patch with an inner surface of the absorbent article, wherein the inner surface is configured to contact a user when in use, and wherein the "C"-shaped pattern of glue is configured to form a pocket configured to retain liquids and solids within the absorbent article when the patch is adhered to the absorbent article.

Embodiment 21. The method of embodiment 2, wherein exactly one continuous sheet of nonwoven material is provided, and wherein the method further comprises, consists essentially of, or consists of:
  after positioning the plurality of elastic strands on the continuous sheet of nonwoven material, folding the continuous sheet of nonwoven material around the plurality of elastic strands,
  wherein the folding is in the CD such that a first longitudinal edge of the continuous sheet of nonwoven material overlaps a second longitudinal edge of the continuous sheet of nonwoven material, thereby forming a seam running in the MD, and
  wherein each elastic strand is positioned between an upper portion of the continuous nonwoven material and a lower portion of the continuous nonwoven material; and
  ultrasonically bonding the seam in the continuous sheet of nonwoven material and the plurality of elastic strands to the folded continuous sheet of nonwoven material such that the plurality of elastic strands is bonded between the upper portion of the continuous nonwoven material and the lower portion of the continuous nonwoven material,
  wherein adhering the patch to the absorbent article comprises, consists essentially of, or consists of:
  providing a plurality of absorbent articles in a machine direction (MD);
  applying glue to a continuous sheet of patch material;
  supplying the continuous sheet of patch material to an alignment wheel;
  cutting the continuous sheet of patch material at regular intervals in a cross-direction (CD) to produce a plurality of patches;
  rotating each patch in the plurality of patches 90°;
  aligning one patch in the plurality of patches with one absorbent article in the plurality of absorbent articles; and
  pressing the patch against the absorbent article,
  wherein aligning the patch with the absorbent article comprises, consists essentially of, or consists of supplying the continuous sheet of patch material to the alignment wheel at a first speed, moving the patch in the MD on the alignment wheel at a second speed, and moving the absorbent article in the MD at a third speed that is equal to the second speed.

Embodiment 22. The method of embodiment 2, wherein exactly one continuous sheet of nonwoven material is provided, and wherein the method further comprises, consists essentially of, or consists of:
  after positioning the plurality of elastic strands on the continuous sheet of nonwoven material, folding the continuous sheet of nonwoven material around the plurality of elastic strands,
  wherein the folding is in the CD such that a first longitudinal edge of the continuous sheet of nonwoven material overlaps a second longitudinal edge of the continuous sheet of nonwoven material, thereby forming a seam running in the MD, and
  wherein each elastic strand is positioned between an upper portion of the continuous nonwoven material and a lower portion of the continuous nonwoven material; and
  thermomechanically bonding the seam in the continuous sheet of nonwoven material and the plurality of elastic strands to the folded continuous sheet of nonwoven material such that the plurality of elastic strands is bonded between the upper portion of the continuous nonwoven material and the lower portion of the continuous nonwoven material,
  wherein adhering the patch to the absorbent article comprises, consists essentially of, or consists of:
  providing a plurality of absorbent articles in a machine direction (MD);
  applying glue to a continuous sheet of patch material;
  supplying the continuous sheet of patch material to an alignment wheel;
  cutting the continuous sheet of patch material at regular intervals in a cross-direction (CD) to produce a plurality of patches;
  rotating each patch in the plurality of patches 90°;
  aligning one patch in the plurality of patches with one absorbent article in the plurality of absorbent articles; and
  pressing the patch against the absorbent article,
  wherein aligning the patch with the absorbent article comprises, consists essentially of, or consists of supplying the continuous sheet of patch material to the alignment wheel at a first speed, moving the patch in the MD on the alignment wheel at a second speed that is greater than the first speed, and moving the absorbent article in the MD at a third speed that is equal to the second speed.

Embodiment 23. The method of embodiment 2, wherein exactly one continuous sheet of nonwoven material is provided, and wherein the method further comprises, consists essentially of, or consists of:
  after positioning the plurality of elastic strands on the continuous sheet of nonwoven material, folding the continuous sheet of nonwoven material around the plurality of elastic strands,
  wherein the folding is in the CD such that a first longitudinal edge of the continuous sheet of nonwoven material overlaps a second longitudinal edge of the continuous sheet of nonwoven material, thereby forming a seam running in the MD, and wherein each elastic strand is positioned between an upper portion of the continuous nonwoven material and a lower portion of the continuous nonwoven material; and gluing the seam in the continuous sheet of nonwoven material and the plurality of elastic strands to the folded continuous sheet of nonwoven material such that the plurality of elastic strands is glued between the upper portion of the continuous nonwoven material and the lower portion of the continuous nonwoven material, wherein adhering the patch to the absorbent article comprises, consists essentially of, or consists of:

providing a plurality of absorbent articles in a machine direction (MD);

applying glue to a continuous sheet of patch material;

supplying the continuous sheet of patch material to an alignment wheel;

cutting the continuous sheet of patch material at regular intervals in a cross-direction (CD) to produce a plurality of patches;

rotating each patch in the plurality of patches 90°;

aligning one patch in the plurality of patches with one absorbent article in the plurality of absorbent articles; and pressing the patch against the absorbent article, wherein aligning the patch with the absorbent article comprises, consists essentially of, or consists of supplying the continuous sheet of patch material to the alignment wheel at a first speed, moving the patch in the MD on the alignment wheel at a second speed, and moving the absorbent article in the MD at a third speed that is equal to the second speed.

Embodiment 24. The method of embodiment 2, wherein first and second continuous sheets of nonwoven material are provided, and wherein the method further comprises, consists essentially of, or consists of:

positioning the plurality of elastic strands between the first continuous sheet of nonwoven material and the second continuous sheet of nonwoven material such that the first continuous sheet of nonwoven material and second continuous sheet of nonwoven material substantially overlap one another;

ultrasonically bonding the plurality of elastic strands between the first continuous sheet of nonwoven material and the second continuous sheet of nonwoven material;

folding a first longitudinal edge of the first continuous sheet of nonwoven material and a first longitudinal edge of the second continuous sheet of nonwoven material, which first longitudinal edges are overlapping, and ultrasonically bonding the folded first longitudinal edges to the first continuous sheet of nonwoven material; and folding a second longitudinal edge of the first continuous sheet of nonwoven material and a second longitudinal edge of the second continuous sheet of nonwoven material, which second longitudinal edges are overlapping, and ultrasonically bonding the folded second longitudinal edges to the first continuous sheet of nonwoven material, wherein adhering the patch to the absorbent article comprises, consists essentially of, or consists of:

providing a plurality of absorbent articles in a machine direction (MD);

applying glue to a continuous sheet of patch material;

supplying the continuous sheet of patch material to an alignment wheel;

cutting the continuous sheet of patch material at regular intervals in a cross-direction (CD) to produce a plurality of patches;

rotating each patch in the plurality of patches 90°;

aligning one patch in the plurality of patches with one absorbent article in the plurality of absorbent articles; and pressing the patch against the absorbent article, wherein aligning the patch with the absorbent article comprises, consists essentially of, or consists of supplying the continuous sheet of patch material to the alignment wheel at a first speed, moving the patch in the MD on the alignment wheel at a second speed that is greater than the first speed, and moving the absorbent article in the MD at a third speed that is equal to the second speed.

Embodiment 25. The method of embodiment 2, wherein first and second continuous sheets of nonwoven material are provided, and wherein the method further comprises, consists essentially of, or consists of:

positioning the plurality of elastic strands between the first continuous sheet of nonwoven material and the second continuous sheet of nonwoven material such that the first continuous sheet of nonwoven material and second continuous sheet of nonwoven material substantially overlap one another;

thermomechanically bonding the plurality of elastic strands between the first continuous sheet of nonwoven material and the second continuous sheet of nonwoven material;

folding a first longitudinal edge of the first continuous sheet of nonwoven material and a first longitudinal edge of the second continuous sheet of nonwoven material, which first longitudinal edges are overlapping, and thermomechanically bonding the folded first longitudinal edges to the first continuous sheet of nonwoven material; and folding a second longitudinal edge of the first continuous sheet of nonwoven material and a second longitudinal edge of the second continuous sheet of nonwoven material, which second longitudinal edges are overlapping, and thermomechanically bonding the folded second longitudinal edges to the first continuous sheet of nonwoven material, wherein adhering the patch to the absorbent article comprises, consists essentially of, or consists of:

providing a plurality of absorbent articles in a machine direction (MD);

applying glue to a continuous sheet of patch material;

supplying the continuous sheet of patch material to an alignment wheel;

cutting the continuous sheet of patch material at regular intervals in a cross-direction (CD) to produce a plurality of patches;

rotating each patch in the plurality of patches 90°;

aligning one patch in the plurality of patches with one absorbent article in the plurality of absorbent articles; and pressing the patch against the absorbent article, wherein aligning the patch with the absorbent article comprises, consists essentially of, or consists of supplying the continuous sheet of patch material to the alignment wheel at a first speed, moving the patch in the MD on the alignment wheel at a second speed that is greater than the first speed, and moving the absorbent article in the MD at a third speed that is equal to the second speed.

Embodiment 26. The method of embodiment 2, wherein first and second continuous sheets of nonwoven material are provided, and wherein the method further comprises, consists essentially of, or consists of:
  positioning the plurality of elastic strands between the first continuous sheet of nonwoven material and the second continuous sheet of nonwoven material such that the first continuous sheet of nonwoven material and second continuous sheet of nonwoven material substantially overlap one another;
  gluing the plurality of elastic strands between the first continuous sheet of nonwoven material and the second continuous sheet of nonwoven material;
  folding a first longitudinal edge of the first continuous sheet of nonwoven material and a first longitudinal edge of the second continuous sheet of nonwoven material, which first longitudinal edges are overlapping, and gluing the folded first longitudinal edges to the first continuous sheet of nonwoven material; and
  folding a second longitudinal edge of the first continuous sheet of nonwoven material and a second longitudinal edge of the second continuous sheet of nonwoven material, which second longitudinal edges are overlapping, and gluing the folded second longitudinal edges to the first continuous sheet of nonwoven material,
  wherein adhering the patch to the absorbent article comprises, consists essentially of, or consists of:
  providing a plurality of absorbent articles in a machine direction (MD);
  applying glue to a continuous sheet of patch material;
  supplying the continuous sheet of patch material to an alignment wheel;
  cutting the continuous sheet of patch material at regular intervals in a cross-direction (CD) to produce a plurality of patches;
  rotating each patch in the plurality of patches 90°;
  aligning one patch in the plurality of patches with one absorbent article in the plurality of absorbent articles; and
  pressing the patch against the absorbent article,
  wherein aligning the patch with the absorbent article comprises, consists essentially of, or consists of supplying the continuous sheet of patch material to the alignment wheel at a first speed, moving the patch in the MD on the alignment wheel at a second speed that is greater than the first speed, and moving the absorbent article in the MD at a third speed that is equal to the second speed.

Embodiment 27. The method of embodiment 2, wherein exactly one continuous sheet of nonwoven material is provided, and wherein the method further comprises, consists essentially of, or consists of:
  after positioning the plurality of elastic strands on the continuous sheet of nonwoven material, folding the continuous sheet of nonwoven material around the plurality of elastic strands,
  wherein the folding is in the CD such that a first longitudinal edge of the continuous sheet of nonwoven material overlaps a second longitudinal edge of the continuous sheet of nonwoven material, thereby forming a seam running in the MD, and
  wherein each elastic strand is positioned between an upper portion of the continuous nonwoven material and a lower portion of the continuous nonwoven material; and
  ultrasonically bonding the seam in the continuous sheet of nonwoven material and the plurality of elastic strands to the folded continuous sheet of nonwoven material such that the plurality of elastic strands is bonded between the upper portion of the continuous nonwoven material and the lower portion of the continuous nonwoven material,
  wherein adhering the patch to the absorbent article comprises, consists essentially of, or consists of:
  providing a plurality of absorbent articles in a machine direction (MD);
  applying glue to a continuous sheet of patch material;
  supplying the continuous sheet of patch material to an alignment wheel;
  cutting the continuous sheet of patch material at regular intervals in a cross-direction (CD) to produce a plurality of patches;
  rotating each patch in the plurality of patches 90°;
  aligning one patch in the plurality of patches with one absorbent article in the plurality of absorbent articles; and
  pressing the patch against the absorbent article,
  wherein aligning the patch with the absorbent article comprises, consists essentially of, or consists of supplying the continuous sheet of patch material to the alignment wheel at a first speed, moving the patch in the MD on the alignment wheel at a second speed equal to the first speed, and moving the absorbent article in the MD at a third speed that is greater than the second speed.

Embodiment 28. The method of embodiment 2, wherein exactly one continuous sheet of nonwoven material is provided, and wherein the method further comprises, consists essentially of, or consists of:
  after positioning the plurality of elastic strands on the continuous sheet of nonwoven material, folding the continuous sheet of nonwoven material around the plurality of elastic strands,
  wherein the folding is in the CD such that a first longitudinal edge of the continuous sheet of nonwoven material overlaps a second longitudinal edge of the continuous sheet of nonwoven material, thereby forming a seam running in the MD, and
  wherein each elastic strand is positioned between an upper portion of the continuous nonwoven material and a lower portion of the continuous nonwoven material; and
  thermomechanically bonding the seam in the continuous sheet of nonwoven material and the plurality of elastic strands to the folded continuous sheet of nonwoven material such that the plurality of elastic strands is bonded between the upper portion of the continuous nonwoven material and the lower portion of the continuous nonwoven material,
  wherein adhering the patch to the absorbent article comprises, consists essentially of, or consists of:
  providing a plurality of absorbent articles in a machine direction (MD);
  applying glue to a continuous sheet of patch material;
  supplying the continuous sheet of patch material to an alignment wheel;
  cutting the continuous sheet of patch material at regular intervals in a cross-direction (CD) to produce a plurality of patches;
  rotating each patch in the plurality of patches 90°;
  aligning one patch in the plurality of patches with one absorbent article in the plurality of absorbent articles; and
  pressing the patch against the absorbent article, wherein aligning the patch with the absorbent article comprises, consists essentially of, or consists of supplying the continuous sheet of patch material to the alignment wheel at a first speed, moving the patch in the MD on the alignment wheel at a second speed equal to the first speed, and moving the absorbent article in the MD at a third speed that is greater than the second speed.

Embodiment 29. The method of embodiment 2, wherein exactly one continuous sheet of nonwoven material is provided, and wherein the method further comprises, consists essentially of, or consists of:
  after positioning the plurality of elastic strands on the continuous sheet of nonwoven material, folding the continuous sheet of nonwoven material around the plurality of elastic strands,
  wherein the folding is in the CD such that a first longitudinal edge of the continuous sheet of nonwoven material overlaps a second longitudinal edge of the continuous sheet of nonwoven material, thereby forming a seam running in the MD, and
  wherein each elastic strand is positioned between an upper portion of the continuous nonwoven material and a lower portion of the continuous nonwoven material; and
  gluing the seam in the continuous sheet of nonwoven material and the plurality of elastic strands to the folded continuous sheet of nonwoven material such that the plurality of elastic strands is glued between the upper portion of the continuous nonwoven material and the lower portion of the continuous nonwoven material,
  wherein adhering the patch to the absorbent article comprises, consists essentially of, or consists of:
  providing a plurality of absorbent articles in a machine direction (MD);
  applying glue to a continuous sheet of patch material;
  supplying the continuous sheet of patch material to an alignment wheel;
  cutting the continuous sheet of patch material at regular intervals in a cross-direction (CD) to produce a plurality of patches;
  rotating each patch in the plurality of patches 90°;
  aligning one patch in the plurality of patches with one absorbent article in the plurality of absorbent articles; and
  pressing the patch against the absorbent article,
  wherein aligning the patch with the absorbent article comprises, consists essentially of, or consists of supplying the continuous sheet of patch material to the alignment wheel at a first speed, moving the patch in the MD on the alignment wheel at a second speed that is equal to the first speed, and moving the absorbent article in the MD at a third speed that is greater than the second speed. Not preferred embodiment (due to yellow part)

Embodiment 30. The method of embodiment 2, wherein first and second continuous sheets of nonwoven material are provided, and wherein the method further comprises, consists essentially of, or consists of:
  positioning the plurality of elastic strands between the first continuous sheet of nonwoven material and the second continuous sheet of nonwoven material such that the first continuous sheet of nonwoven material and second continuous sheet of nonwoven material substantially overlap one another;
  ultrasonically bonding the plurality of elastic strands between the first continuous sheet of nonwoven material and the second continuous sheet of nonwoven material;
  folding a first longitudinal edge of the first continuous sheet of nonwoven material and a first longitudinal edge of the second continuous sheet of nonwoven material, which first longitudinal edges are overlapping, and ultrasonically bonding the folded first longitudinal edges to the first continuous sheet of nonwoven material; and
  folding a second longitudinal edge of the first continuous sheet of nonwoven material and a second longitudinal edge of the second continuous sheet of nonwoven material, which second longitudinal edges are overlapping, and ultrasonically bonding the folded second longitudinal edges to the first continuous sheet of nonwoven material,
  wherein adhering the patch to the absorbent article comprises, consists essentially of, or consists of:
  providing a plurality of absorbent articles in a machine direction (MD);
  applying glue to a continuous sheet of patch material;
  supplying the continuous sheet of patch material to an alignment wheel;
  cutting the continuous sheet of patch material at regular intervals in a cross-direction (CD) to produce a plurality of patches;
  rotating each patch in the plurality of patches 90°;
  aligning one patch in the plurality of patches with one absorbent article in the plurality of absorbent articles; and
  pressing the patch against the absorbent article,
  wherein aligning the patch with the absorbent article comprises, consists essentially of, or consists of supplying the continuous sheet of patch material to the alignment wheel at a first speed, moving the patch in the MD on the alignment wheel at a second speed that is equal to the first speed, and moving the absorbent article in the MD at a third speed that is greater than the second speed.

Embodiment 31. The method of embodiment 2, wherein first and second continuous sheets of nonwoven material are provided, and wherein the method further comprises, consists essentially of, or consists of:
  positioning the plurality of elastic strands between the first continuous sheet of nonwoven material and the second continuous sheet of nonwoven material such that the first continuous sheet of nonwoven material and second continuous sheet of nonwoven material substantially overlap one another;
  thermomechanically bonding the plurality of elastic strands between the first continuous sheet of nonwoven material and the second continuous sheet of nonwoven material;
  folding a first longitudinal edge of the first continuous sheet of nonwoven material and a first longitudinal edge of the second continuous sheet of nonwoven material, which first longitudinal edges are overlapping, and thermomechanically bonding the folded first longitudinal edges to the first continuous sheet of nonwoven material; and
  folding a second longitudinal edge of the first continuous sheet of nonwoven material and a second longitudinal edge of the second continuous sheet of nonwoven material, which second longitudinal edges are overlapping, and thermomechanically bonding the folded second longitudinal edges to the first continuous sheet of nonwoven material, wherein adhering the patch to the absorbent article comprises, consists essentially of, or consists of:

providing a plurality of absorbent articles in a machine direction (MD);

applying glue to a continuous sheet of patch material;

supplying the continuous sheet of patch material to an alignment wheel;

cutting the continuous sheet of patch material at regular intervals in a cross-direction (CD) to produce a plurality of patches;

rotating each patch in the plurality of patches 90°;

aligning one patch in the plurality of patches with one absorbent article in the plurality of absorbent articles; and pressing the patch against the absorbent article, wherein aligning the patch with the absorbent article comprises, consists essentially of, or consists of supplying the continuous sheet of patch material to the alignment wheel at a first speed, moving the patch in the MD on the alignment wheel at a second speed that is equal to the first speed, and moving the absorbent article in the MD at a third speed that is greater than the second speed.

Embodiment 32. The method of embodiment 2, wherein first and second continuous sheets of nonwoven material are provided, and wherein the method further comprises, consists essentially of, or consists of:

positioning the plurality of elastic strands between the first continuous sheet of nonwoven material and the second continuous sheet of nonwoven material such that the first continuous sheet of nonwoven material and second continuous sheet of nonwoven material substantially overlap one another;

gluing the plurality of elastic strands between the first continuous sheet of nonwoven material and the second continuous sheet of nonwoven material;

folding a first longitudinal edge of the first continuous sheet of nonwoven material and a first longitudinal edge of the second continuous sheet of nonwoven material, which first longitudinal edges are overlapping, and gluing the folded first longitudinal edges to the first continuous sheet of nonwoven material; and folding a second longitudinal edge of the first continuous sheet of nonwoven material and a second longitudinal edge of the second continuous sheet of nonwoven material, which second longitudinal edges are overlapping, and gluing the folded second longitudinal edges to the first continuous sheet of nonwoven material, wherein adhering the patch to the absorbent article comprises, consists essentially of, or consists of:

providing a plurality of absorbent articles in a machine direction (MD);

applying glue to a continuous sheet of patch material;

supplying the continuous sheet of patch material to an alignment wheel;

cutting the continuous sheet of patch material at regular intervals in a cross-direction (CD) to produce a plurality of patches;

rotating each patch in the plurality of patches 90°;

aligning one patch in the plurality of patches with one absorbent article in the plurality of absorbent articles; and pressing the patch against the absorbent article, wherein aligning the patch with the absorbent article comprises, consists essentially of, or consists of supplying the continuous sheet of patch material to the alignment wheel at a first speed, moving the patch in the MD on the alignment wheel at a second speed that is equal to the first speed, and moving the absorbent article in the MD at a third speed that is greater than the second speed.

Apparatuses for producing absorbent articles.

Embodiment 33. An apparatus for producing an absorbent article having a pocket comprising, consisting essentially of, or consisting of:

a patch-forming module configured to form a continuous sheet of patch material that comprises at least one nonwoven layer and a plurality of elastic strands bonded to the at least one nonwoven layer;

a primary glue applicator configured to apply glue to the continuous sheet of patch material, wherein the primary glue applicator is configured to apply glue in a pattern including an adhering portion and a non-adhering portion, the non-adhering portion partially bounded by the adhering portion;

a cut-and-turn wheel comprising, consisting essentially of, or consisting of a plurality of rotatable vacuum pucks configured to accept the continuous sheet of patch material;

a cutting wheel having a plurality of blades configured to rotate coincident to the cut-and-turn wheel, wherein the cutting wheel is configured to cut the continuous sheet of patch material at regular intervals to form a plurality of patches, wherein each patch in the plurality of patches is affixed to one of the rotatable vacuum pucks, and wherein each rotatable vacuum puck is configured to rotate the corresponding patch by 900 after cutting;

a conveyor configured to supply a plurality of absorbent articles, wherein the conveyor is configured such that each absorbent article is positioned adjacent to a patch after the patch has been rotated by the rotatable vacuum puck; and a phased roll having an oval shape with a major diameter and a minor diameter, the phased roll positioned adjacent to the absorbent article and configured to apply pressure with the major diameter on each absorbent article when positioned next to a patch thereby effectuating adhesion of the patch to the absorbent article, wherein the glue pattern, when the patch is adhered to the absorbent article, produces a pocket accessible via the non-adhering portion of the glue pattern.

Embodiment 34. The apparatus of embodiment 33, wherein the primary glue applicator is configured to apply glue continuously across a first portion of the continuous sheet of patch material and to apply glue intermittently at regular intervals across a second portion of the continuous sheet of patch material, wherein the first portion is adjacent to the second portion in the cross-direction (CD).

Embodiment 35. The apparatus of embodiment 33, wherein the primary glue applicator is configured to apply glue in a "C"-shaped pattern.

Embodiment 36. The apparatus of embodiment 34, wherein cutting the continuous sheet of patch material comprises, consists essentially of, or consists of cutting each intermittently applied amount of glue in the second portion in approximately two equal sizes so that a "C"-shaped pattern of glue is present on each patch in the plurality of patches.

Embodiment 37. The apparatus of embodiment 33, wherein the primary glue applicator applies glue to a first side of the continuous sheet of match material, and the cut-and-turn wheel accepts the continuous sheet of patch material such that the plurality of rotatable vacuum pucks contact a second side of the continuous sheet of patch material.

Embodiment 38. The apparatus of embodiment 33, wherein the patch-forming module comprises, consists essentially of, or consists of:
- a folding chute configured to receive a continuous sheet of nonwoven material in a machine direction (MD) and a plurality of elastic strands in the MD, wherein the folding chute is configured to fold a first longitudinal edge of the continuous sheet of nonwoven material in a cross-direction and a second longitudinal edge of the continuous sheet of nonwoven material in the cross-direction such that the first longitudinal edge and the second longitudinal edge enclose the plurality of elastic strands and overlap one another so that a seam is formed running in the MD.

Embodiment 39. The apparatus of embodiment 38, wherein the patch-forming module further comprises, consists essentially of, or consists of:
- a rotating anvil configured to receive the folded continuous sheet of nonwoven material; and
- an ultrasonic horn configured to intermittently press the folded continuous sheet of nonwoven material against the rotating anvil in order to ultrasonically bond the plurality of elastic strands within the folded continuous sheet of nonwoven material, and to ultrasonically bond the seam, thereby forming the continuous sheet of patch material.

Embodiment 40. The apparatus of embodiment 39, wherein the rotating anvil has a plurality of rows of protrusions extending across a surface of the rotating anvil, each row of protrusions extending from a first edge of the rotating anvil to a second edge of the rotating anvil in a cross-direction (CD),
- wherein each row extends across the surface of the rotating anvil in a "zig-zag" pattern such that every circumferential position on the anvil row includes at least one protrusion from one of the plurality of rows of protrusions,
- wherein adjacent protrusions are separated by a distance configured to entrap an elastic strand bonded therebetween.

Embodiment 41. The apparatus of embodiment 39, wherein the rotating anvil has a plurality of rows of protrusions extending across a surface of the rotating anvil, each row of protrusions extending from a first edge of the rotating anvil to a second edge of the rotating anvil in a cross-direction (CD),
- wherein each row of protrusions extends across the surface of the rotating anvil in a direction orthogonal to a circumferential axis of the rotating anvil,
- wherein each row of protrusions comprises, consists essentially of, or consists of a plurality of bond protrusion pairs, each bond protrusion pair comprising, consisting essentially of, or consisting of a first protrusion and a second protrusion separated by a distance configured to entrap an elastic strand therebetween in a tensioned state, and
- wherein each row of protrusions comprises, consists essentially of, or consists of a plurality of non-bonding protrusion pairs, each non-bonding protrusion pairs comprising, consisting essentially of, or consisting of a first protrusion and a second protrusion separated by a distance configured to permit an elastic strand positioned therebetween to tension and relax without restriction.

Embodiment 42. The apparatus of embodiment 38, wherein the patch-forming module further comprises, consists essentially of, or consists of:
- a rotating anvil configured to receive the folded continuous sheet of nonwoven material; and
- a heated roll positioned adjacent to and in contact with the rotating anvil configured to thermomechanically seal the plurality of elastic strands within the folded continuous sheet of nonwoven material, and to thermomechanically seal the seam, thereby forming the continuous sheet of patch material.

Embodiment 43. The apparatus of embodiment 42, wherein the rotating anvil has a plurality of rows of protrusions extending across a surface of the rotating anvil, each row of protrusions extending from a first edge of the rotating anvil to a second edge of the rotating anvil in a cross-direction (CD),
- wherein each row of protrusions extends across the surface of the rotating angle in a direction orthogonal to a circumferential axis of the rotating angle,
- wherein each row of protrusions comprises, consists essentially of, or consists of a plurality of bond protrusion pairs, each bond protrusion pair comprising, consisting essentially of, or consisting of a first protrusion and a second protrusion separated by a distance configured to entrap an elastic strand therebetween in a tensioned state, and
- wherein each row of protrusions comprises, consists essentially of, or consists of a plurality of non-bonding protrusion pairs, each non-bonding protrusion pairs comprising, consisting essentially of, or consisting of a first protrusion and a second protrusion separated by a distance configured to permit an elastic strand positioned therebetween to tension and relax without restriction.

Embodiment 44. The apparatus of embodiment 38, wherein the patch-forming module further comprises, consists essentially of, or consists of:
- a first glue applicator configured to apply glue to the plurality of elastic strands before entering the folding chute;
- a second glue applicator configured to apply glue to the first longitudinal edge and the second longitudinal edge of the continuous sheet of nonwoven material before entering the folding chute; and
- a pair of pressing rolls configured to press the folded continuous sheet of nonwoven material together in order to effectuate adhesion of the plurality of elastic strands within the folded continuous sheet of nonwoven material, and to effectuate adhesion of the seam, thereby forming the continuous sheet of patch material.

Embodiment 45. The apparatus of embodiment 33, wherein the patch-forming module comprises, consists essentially of, or consists of:
- a slitter configured to accept a continuous source of nonwoven material and slit the continuous source of nonwoven material into a first continuous sheet of nonwoven material and a second continuous source of nonwoven material;
- a first steering guide configured to accept the first continuous sheet of nonwoven material;
- a second steering guide configured to accept the second continuous sheet of nonwoven material, wherein the first and second steering guides align the first and second continuous sheets of nonwoven material with one another; and a third steering guide configured to accept a plurality of elastic strands and align the plurality of elastic strands between the first and second continuous sheets of nonwoven material.

Embodiment 46. The apparatus of embodiment 45, wherein the patch-forming module further comprises, consists essentially of, or consists of:

a rotating anvil configured to receive the first continuous sheet of nonwoven material, the plurality of elastic strands, and the second continuous sheet of nonwoven material;

an ultrasonic horn configured to intermittently press the first continuous sheet of nonwoven material, the plurality of elastic strands, and the second continuous sheet of nonwoven material against the rotating anvil in order to ultrasonically bond the plurality of elastic strands within the first and second continuous sheets of nonwoven material to form a continuous sheet of bonded elastic nonwoven material;

a folding chute configured to receive the continuous sheet of bonded elastic nonwoven material in a machine direction (MD), wherein the folding chute is configured to fold a first longitudinal edge of the continuous sheet of bonded elastic nonwoven material in a cross-direction and a second longitudinal edge of the continuous sheet of bonded elastic nonwoven material in the cross-direction;

a rotating anvil configured to receive the folded continuous sheet of bonded elastic nonwoven material; and a heated roll positioned adjacent to and in contact with the rotating anvil configured to thermomechanically seal the first and second folded longitudinal edges, thereby forming the continuous sheet of patch material.

Embodiment 47. The apparatus of embodiment 46, wherein the rotating anvil has a plurality of rows of protrusions extending across a surface of the rotating anvil, each row of protrusions extending from a first edge of the rotating anvil to a second edge of the rotating anvil in a cross-direction (CD), wherein each row extends across the surface of the rotating anvil in a "zig-zag" pattern such that every circumferential position on the anvil row includes at least one protrusion from one of the plurality of rows of protrusions, wherein adjacent protrusions are separated by a distance configured to entrap an elastic strand bonded therebetween.

Embodiment 48. The apparatus of embodiment 46, wherein the rotating anvil has a plurality of rows of protrusions extending across a surface of the rotating anvil, each row of protrusions extending from a first edge of the rotating anvil to a second edge of the rotating anvil in a cross-direction (CD), wherein each row of protrusions extends across the surface of the rotating angle in a direction orthogonal to a circumferential axis of the rotating angle, wherein each row of protrusions comprises, consists essentially of, or consists of a plurality of bond protrusion pairs, each bond protrusion pair comprising, consisting essentially of, or consisting of a first protrusion and a second protrusion separated by a distance configured to entrap an elastic strand therebetween in a tensioned state, and wherein each row of protrusions comprises, consists essentially of, or consists of a plurality of non-bonding protrusion pairs, each non-bonding protrusion pairs comprising, consisting essentially of, or consisting of a first protrusion and a second protrusion separated by a distance configured to permit an elastic strand positioned therebetween to tension and relax without restriction.

Embodiment 49. The apparatus of embodiment 45, wherein the patch-forming module further comprises, consists essentially of, or consists of:

a first rotating anvil configured to receive the first continuous sheet of nonwoven material, the plurality of elastic strands, and the second continuous sheet of nonwoven material;

a first heated roll positioned adjacent to and in contact with the first rotating anvil configured to thermomechanically seal the first continuous sheet of nonwoven material, the plurality of elastic strands, and the second continuous sheet of nonwoven material together, thereby bonding the plurality of elastic strands within the first and second continuous sheets of nonwoven material to form a continuous sheet of bonded elastic nonwoven material;

a folding chute configured to receive the continuous sheet of bonded elastic nonwoven material in a machine direction (MD), wherein the folding chute is configured to fold a first longitudinal edge of the continuous sheet of bonded elastic nonwoven material in a cross-direction and a second longitudinal edge of the continuous sheet of bonded elastic nonwoven material in the cross-direction;

a second rotating anvil configured to receive the folded continuous sheet of bonded elastic nonwoven material; and a second heated roll positioned adjacent to and in contact with the second rotating anvil configured to thermomechanically seal the first and second folded longitudinal edges, thereby forming the continuous sheet of patch material.

Embodiment 50. The apparatus of embodiment 49, wherein the first rotating anvil has a plurality of rows of protrusions extending across a surface of the first rotating anvil, each row of protrusions extending from a first edge of the first rotating anvil to a second edge of the first rotating anvil in a cross-direction (CD), wherein each row of protrusions extends across the surface of the first rotating angle in a direction orthogonal to a circumferential axis of the rotating angle, wherein each row of protrusions comprises, consists essentially of, or consists of a plurality of bond protrusion pairs, each bond protrusion pair comprising, consisting essentially of, or consisting of a first protrusion and a second protrusion separated by a distance configured to entrap an elastic strand therebetween in a tensioned state, and wherein each row of protrusions comprises, consists essentially of, or consists of a plurality of non-bonding protrusion pairs, each non-bonding protrusion pairs comprising, consisting essentially of, or consisting of a first protrusion and a second protrusion separated by a distance configured to permit an elastic strand positioned therebetween to tension and relax without restriction.

Embodiment 51. The apparatus of embodiment 49, wherein the second rotating anvil has a plurality of rows of protrusions extending across a surface of the second rotating anvil, each row of protrusions extending from a first edge of the second rotating anvil to a second edge of the second rotating anvil in a cross-direction (CD),
    wherein each row of protrusions extends across the surface of the second rotating angle in a direction orthogonal to a circumferential axis of the second rotating angle,
    wherein each row of protrusions comprises, consists essentially of, or consists of a plurality of bond protrusion pairs, each bond protrusion pair comprising, consisting essentially of, or consisting of a first protrusion and a second protrusion separated by a distance configured to entrap an elastic strand therebetween in a tensioned state, and
    wherein each row of protrusions comprises, consists essentially of, or consists of a plurality of non-bonding protrusion pairs, each non-bonding protrusion pairs comprising, consisting essentially of, or consisting of a first protrusion and a second protrusion separated by a distance configured to permit an elastic strand positioned therebetween to tension and relax without restriction.

Embodiment 52. The apparatus of embodiment 45, wherein the patch-forming module further comprises, consists essentially of, or consists of:
    a first glue applicator configured to apply glue to the plurality of elastic strands after the third steering guide;
    a first pair of pressing rolls configured to press and to effectuate adhesion of the first continuous sheet of nonwoven material, the plurality of elastic strands, and the second continuous sheet of nonwoven material, thereby forming a continuous sheet of glued elastic nonwoven material;
    a second glue applicator configured to apply glue to a first longitudinal edge and a second longitudinal edge of the continuous sheet of glued elastic nonwoven material;
    a folding chute configured to receive the continuous sheet of glued elastic nonwoven material in a machine direction (MD), wherein the folding chute is configured to fold a first longitudinal edge of the continuous sheet of bonded elastic nonwoven material in a cross-direction (CD) and a second longitudinal edge of the continuous sheet of bonded elastic nonwoven material in the CD;
    a second pair of pressing rolls configured to press the folded continuous sheet of glued elastic nonwoven material together in order to effectuate adhesion of the first and second folded longitudinal edges, thereby forming the continuous sheet of patch material.

Absorbent articles having pockets.

Embodiment 53. An absorbent article having a pocket, the absorbent article comprises, consists essentially of, or consists of:
    an absorbent article; and
    a patch adhered to the absorbent article, wherein the patch is adhered using a glue pattern comprising a non-adhesion region partially bound by an adhesion region so that a pocket is formed.

Embodiment 54. The absorbent article of embodiment 53, wherein the glue pattern is a "C"-shaped glue pattern.

Embodiment 55. The absorbent article of embodiment 53, wherein the patch comprises, consists essentially of, or consists of at least one piece of nonwoven material and a plurality of elastic strands bonded to the at least one piece of nonwoven material.

Embodiment 56. The absorbent article of embodiment 55, wherein the plurality of elastic strands are bonded to the at least one piece of nonwoven material using ultrasonic bonding, thermomechanical bonding, and/or glue.

Embodiment 57. The absorbent article of embodiment 56, wherein the bonding is ultrasonic or thermomechanical bonding, and wherein the plurality of elastic strands are bonded to the at least one piece of nonwoven material using a bond pattern comprising, consisting essentially of, or consisting of a plurality of rows of bonds extending from a first longitudinal edge of the patch to a second longitudinal edge of the patch, each row of bonds having a "zig-zag" pattern such that every lateral position on the patch includes at least one bond from one of the plurality of rows of bonds,
    wherein adjacent bonds in each row of bonds is separated by a distance configured to entrap an elastic strand bonded therebetween.

Embodiment 58. The absorbent article of embodiment 57, wherein only a portion of the bonds entrap an elastic strand.

Embodiment 59. The absorbent article of embodiment 55, wherein the patch comprises, consists essentially of, or consists of exactly one piece of nonwoven material that has been folded around the plurality of elastic strands and bonded at a seam, wherein the seam is bonded using ultrasonic bonding, thermomechanical bonding, and/or glue.

Embodiment 60. The absorbent article of embodiment 55, wherein the patch comprises, consists essentially of, or consists of a first piece of nonwoven material and a second piece of nonwoven material, wherein the plurality of elastic strands are bonded between the first and second pieces of nonwoven material, and wherein the first and second pieces of nonwoven material are bonded together at a first longitudinal edge and a second longitudinal edge, wherein the first and second longitudinal edges are bonded using ultrasonic bonding, thermomechanical bonding, and/or glue.

Embodiment 61. The absorbent article of embodiment 53, wherein the patch is adhered to an inner surface of the absorbent article so the patch is configured to contact a user when the absorbent article is worn.

Embodiment 62. The absorbent article of embodiment 53, wherein the patch is positioned proximal to a first lateral edge of the absorbent article such that an opening formed by the glue pattern is facing a second lateral edge of the absorbent article.

While the disclosure has been described with reference to a number of embodiments, it will be understood by those skilled in the art that the disclosure is not limited to such embodiments. Rather, the disclosure can be modified to incorporate any number of variations, alterations, substitutions, or equivalent arrangements not described herein, but which are commensurate with the spirt and scope of the disclosure. Conditional language used herein, such as "can," "could," "might," or "may," unless specifically stated otherwise, or otherwise understood within the context as used, generally is intended to convey that certain embodiments include, while other embodiments do not include, certain features, elements or functional capabilities. Additionally, while various embodiments of the disclosure have been described, it is to be understood that aspects of the disclosure may include only some of the described embodiments. Accordingly, the disclosure it not to be seen as limited by the foregoing described, but is only limited by the scope of the appended claims.

That which is claimed is:

1. A method for producing an absorbent article having a pocket, the method comprising:
    producing a patch, the patch comprising at least one nonwoven layer and a plurality of elastic strands bonded to the at least nonwoven layer, wherein producing the patch comprises:
providing at least one continuous sheet of nonwoven material in a machine direction (MD);
providing a plurality of elastic strands in the MD and positioning the plurality of elastic strands on the at least one continuous sheet of nonwoven material;
bonding the plurality of elastic strands to the at least one continuous sheet of nonwoven material to form a continuous sheet of patch material; and
cutting the continuous sheet of patch material at regular intervals in a cross-direction (CD) to produce a plurality of patches, and
adhering the patch to an absorbent article to form a pocket, wherein adhering the patch to the absorbent article comprises:
applying glue to a continuous sheet of patch material by moving the continuous sheet of patch material in the MD across a glue applicator, wherein the glue applicator is configured to apply glue continuously across a first portion of the continuous sheet of patch material and to apply glue intermittently across a second portion of the continuous sheet of patch material,
cutting the continuous sheet of patch material to produce a plurality of patches, and
pressing a patch from the plurality of patches against the absorbent article.

2. The method of claim 1, wherein exactly one continuous sheet of nonwoven material is provided, and wherein the method further comprises:
after positioning the plurality of elastic strands on the continuous sheet of nonwoven material, folding the continuous sheet of nonwoven material around the plurality of elastic strands,
wherein the folding is in the CD such that a first longitudinal edge of the continuous sheet of nonwoven material overlaps a second longitudinal edge of the continuous sheet of nonwoven material, thereby forming a seam running in the MD, and
wherein each elastic strand is positioned between an upper portion of the continuous nonwoven material and a lower portion of the continuous nonwoven material; and
bonding the seam in the continuous sheet of nonwoven material and the plurality of elastic strands to the folded continuous sheet of nonwoven material such that the plurality of elastic strands is bonded between the upper portion of the continuous nonwoven material and the lower portion of the continuous nonwoven material.

3. The method of claim 1, wherein first and second continuous sheets of nonwoven material are provided, and wherein the method further comprises:
positioning the plurality of elastic strands between the first continuous sheet of nonwoven material and the second continuous sheet of nonwoven material such that the first continuous sheet of nonwoven material and second continuous sheet of nonwoven material substantially overlap one another;
bonding the plurality of elastic strands between the first continuous sheet of nonwoven material and the second continuous sheet of nonwoven material;
folding a first longitudinal edge of the first continuous sheet of nonwoven material and a first longitudinal edge of the second continuous sheet of nonwoven material, which first longitudinal edges are overlapping, and bonding the folded first longitudinal edges to the first continuous sheet of nonwoven material; and
folding a second longitudinal edge of the first continuous sheet of nonwoven material and a second longitudinal edge of the second continuous sheet of nonwoven material, which second longitudinal edges are overlapping, and bonding the folded second longitudinal edges to the first continuous sheet of nonwoven material.

4. The method of claim 1, wherein the bonding is thermobonding or ultrasonic bonding, and wherein bonding the plurality of elastic strands comprises forming a plurality of bond pairs, each bond pair comprising a first bond and a second bond separated by a distance configured to entrap an elastic strand therebetween in a tensioned state.

5. The method of claim 4, wherein bonding the plurality of elastic strands further comprises forming a plurality of non-bonding pairs, each non-bonding pair comprising a first bond and a second bond separated by a distance configured to permit an elastic strand positioned therebetween to tension and relax without restriction.

6. The method of claim 4, wherein a portion of the plurality of bond pairs do not have an elastic strand entrapped therebetween.

7. The method of claim 1, wherein the plurality of elastic strands are intermittently bonded to the at least one continuous sheet of nonwoven material such that, after cutting the continuous sheet of nonwoven material, the patch has a first lateral edge without bonds, a central portion with bonds, and a second lateral edge without bonds.

8. The method of claim 1, wherein adhering the patch to the absorbent article further comprises:
providing a plurality of absorbent articles in a machine direction (MD);
applying the glue to the continuous sheet of patch material;
supplying the continuous sheet of patch material to an alignment wheel;
cutting the continuous sheet of patch material to produce the plurality of patches;
rotating each patch in the plurality of patches 90°;
aligning one patch in the plurality of patches with one absorbent article in the plurality of absorbent articles; and
pressing the patch against the absorbent article.

9. The method of claim 8, wherein applying glue to the continuous sheet of patch material comprises cutting each intermittently applied amount of glue in the second portion in approximately two equal sizes so that a "C"-shaped pattern of glue is present on each patch in the plurality of patches.

10. The method of claim 8, wherein aligning the patch with the absorbent article comprises supplying the continuous sheet of patch material to the alignment wheel at a first speed, moving the patch in the MD on the alignment wheel at a second speed, and moving the absorbent article in the MD at a third speed.

11. The method of claim 10, wherein the second speed is equal to the third speed such that the elastic patch is unstretched in the MD when pressed against the absorbent article.

12. The method of claim 10, wherein the first speed is equal to the second speed and the second speed is lower than the third speed such that the elastic patch is stretched when pressed against the absorbent article.

13. The method of claim 8, wherein aligning the patch with the absorbent article comprises aligning the patch with an inner surface of the absorbent article, wherein the inner surface is configured to contact a user when in use, and wherein the "C"-shaped pattern of glue is configured to form a pocket configured to retain liquids and solids within the absorbent article when the patch is adhered to the absorbent article.

14. The method of claim 1,
wherein exactly one continuous sheet of nonwoven material is provided, and wherein the method further comprises:
after positioning the plurality of elastic strands on the continuous sheet of nonwoven material, folding the continuous sheet of nonwoven material around the plurality of elastic strands,
wherein the folding is in the CD such that a first longitudinal edge of the continuous sheet of nonwoven material overlaps a second longitudinal edge of the continuous sheet of nonwoven material, thereby forming a seam running in the MD, and
wherein each elastic strand is positioned between an upper portion of the continuous nonwoven material and a lower portion of the continuous nonwoven material; and
ultrasonically bonding the seam in the continuous sheet of nonwoven material and the plurality of elastic strands to the folded continuous sheet of nonwoven material such that the plurality of elastic strands is bonded between the upper portion of the continuous nonwoven material and the lower portion of the continuous nonwoven material,
wherein adhering the patch to the absorbent article comprises:
providing a plurality of absorbent articles in a machine direction (MD);
applying glue to a continuous sheet of patch material;
supplying the continuous sheet of patch material to an alignment wheel;
cutting the continuous sheet of patch material at regular intervals in a cross-direction (CD) to produce a plurality of patches;
rotating each patch in the plurality of patches 90°;
aligning one patch in the plurality of patches with one absorbent article in the plurality of absorbent articles; and
pressing the patch against the absorbent article,
wherein aligning the patch with the absorbent article comprises supplying the continuous sheet of patch material to the alignment wheel at a first speed, moving the patch in the MD on the alignment wheel, and moving the absorbent article in the MD at a third speed that is equal to the second speed.

15. The method of claim 1,
wherein exactly one continuous sheet of nonwoven material is provided, and wherein the method further comprises:
after positioning the plurality of elastic strands on the continuous sheet of nonwoven material, folding the continuous sheet of nonwoven material around the plurality of elastic strands,
wherein the folding is in the CD such that a first longitudinal edge of the continuous sheet of nonwoven material overlaps a second longitudinal edge of the continuous sheet of nonwoven material, thereby forming a seam running in the MD, and
wherein each elastic strand is positioned between an upper portion of the continuous nonwoven material and a lower portion of the continuous nonwoven material; and
gluing the seam in the continuous sheet of nonwoven material and the plurality of elastic strands to the folded continuous sheet of nonwoven material such that the plurality of elastic strands is glued between the upper portion of the continuous nonwoven material and the lower portion of the continuous nonwoven material,
wherein adhering the patch to the absorbent article comprises:
providing a plurality of absorbent articles in a machine direction (MD);
applying glue to a continuous sheet of patch material;
supplying the continuous sheet of patch material to an alignment wheel;
cutting the continuous sheet of patch material at regular intervals in a cross-direction (CD) to produce a plurality of patches;
rotating each patch in the plurality of patches 90°;
aligning one patch in the plurality of patches with one absorbent article in the plurality of absorbent articles; and
pressing the patch against the absorbent article,
wherein aligning the patch with the absorbent article comprises supplying the continuous sheet of patch material to the alignment wheel at a first speed, moving the patch in the MD on the alignment wheel at a second speed, and moving the absorbent article in the MD at a third speed that is equal to the second speed.

16. The method of claim 1,
wherein exactly one continuous sheet of nonwoven material is provided, and wherein the method further comprises:
after positioning the plurality of elastic strands on the continuous sheet of nonwoven material, folding the continuous sheet of nonwoven material around the plurality of elastic strands,
wherein the folding is in the CD such that a first longitudinal edge of the continuous sheet of nonwoven material overlaps a second longitudinal edge of the continuous sheet of nonwoven material, thereby forming a seam running in the MD, and
wherein each elastic strand is positioned between an upper portion of the continuous nonwoven material and a lower portion of the continuous nonwoven material; and
ultrasonically bonding the seam in the continuous sheet of nonwoven material and the plurality of elastic strands to the folded continuous sheet of nonwoven material such that the plurality of elastic strands is bonded between the upper portion of the continuous nonwoven material and the lower portion of the continuous nonwoven material,
wherein adhering the patch to the absorbent article comprises:
providing a plurality of absorbent articles in a machine direction (MD);
applying glue to a continuous sheet of patch material;
supplying the continuous sheet of patch material to an alignment wheel;

cutting the continuous sheet of patch material at regular intervals in a cross-direction (CD) to produce a plurality of patches;
rotating each patch in the plurality of patches 90°;
aligning one patch in the plurality of patches with one absorbent article in the plurality of absorbent articles; and
pressing the patch against the absorbent article,
wherein aligning the patch with the absorbent article comprises supplying the continuous sheet of patch material to the alignment wheel at a first speed, moving the patch in the MD on the alignment wheel at a second speed equal to the first speed, and moving the absorbent article in the MD at a third speed.

17. The method of claim 1,
wherein exactly one continuous sheet of nonwoven material is provided, and wherein the method further comprises:
after positioning the plurality of elastic strands on the continuous sheet of nonwoven material, folding the continuous sheet of nonwoven material around the plurality of elastic strands,
wherein the folding is in the CD such that a first longitudinal edge of the continuous sheet of nonwoven material overlaps a second longitudinal edge of the continuous sheet of nonwoven material, thereby forming a seam running in the MD, and
wherein each elastic strand is positioned between an upper portion of the continuous nonwoven material and a lower portion of the continuous nonwoven material; and
gluing the seam in the continuous sheet of nonwoven material and the plurality of elastic strands to the folded continuous sheet of nonwoven material such that the plurality of elastic strands is glued between the upper portion of the continuous nonwoven material and the lower portion of the continuous nonwoven material,
wherein adhering the patch to the absorbent article comprises:
providing a plurality of absorbent articles in a machine direction (MD);
applying glue to a continuous sheet of patch material;
supplying the continuous sheet of patch material to an alignment wheel;
cutting the continuous sheet of patch material at regular intervals in a cross-direction (CD) to produce a plurality of patches;
rotating each patch in the plurality of patches 90°;
aligning one patch in the plurality of patches with one absorbent article in the plurality of absorbent articles; and
pressing the patch against the absorbent article,
wherein aligning the patch with the absorbent article comprises supplying the continuous sheet of patch material to the alignment wheel at a first speed, moving the patch in the MD on the alignment wheel at a second speed that is equal to the first speed, and moving the absorbent article in the MD at a third speed.

* * * * *